US009775692B2

(12) United States Patent
Thomas et al.

(10) Patent No.: US 9,775,692 B2
(45) Date of Patent: Oct. 3, 2017

(54) ORAL IRRIGATOR WITH VARIABLE PRESSURE

(71) Applicant: WATER PIK, INC., Fort Collins, CO (US)

(72) Inventors: Brenda Lee Thomas, Windsor, CO (US); Kurt Michael Taylor, Fort Collins, CO (US)

(73) Assignee: WATER PIK, INC., Fort Collins, CO (US)

( * ) Notice: Subject to any disclaimer, the term of this patent is extended or adjusted under 35 U.S.C. 154(b) by 394 days.

(21) Appl. No.: 14/262,131

(22) Filed: Apr. 25, 2014

(65) Prior Publication Data

US 2014/0227659 A1    Aug. 14, 2014

Related U.S. Application Data

(63) Continuation of application No. 13/566,652, filed on Aug. 3, 2012, now abandoned, which is a continuation of application No. 12/709,677, filed on Feb. 22, 2010, now Pat. No. 8,403,665, which is a continuation of application No. 11/483,376, filed on Jul. 7, 2006, now Pat. No. 7,670,141.

(51) Int. Cl.
*A61C 17/02* (2006.01)
*A61C 17/028* (2006.01)

(52) U.S. Cl.
CPC ...... *A61C 17/0202* (2013.01); *A61C 17/0205* (2013.01); *A61C 17/028* (2013.01)

(58) Field of Classification Search
CPC ...... A61H 13/005; A61C 17/00; A61C 17/02; A61C 17/0202; A61C 17/0214; A61C 17/0217; A61C 17/028; F16K 13/00; F16K 17/34; Y10T 137/7784
USPC .............................. 251/325; 138/42, 43, 46
See application file for complete search history.

(56) References Cited

U.S. PATENT DOCUMENTS

| 555,588 | A | 3/1896 | Spencer |
|---|---|---|---|
| 1,278,225 | A | 9/1918 | Schamberg |
| 1,464,419 | A | 8/1923 | Gill |
| 1,498,267 | A | 6/1924 | Hachman |

(Continued)

FOREIGN PATENT DOCUMENTS

| CA | 851479 | | 9/1970 |
|---|---|---|---|
| CH | 502817 | A | 2/1971 |

(Continued)

OTHER PUBLICATIONS

US RE27,274, 01/1972, Mattingly (withdrawn)

(Continued)

*Primary Examiner* — Justine Yu
*Assistant Examiner* — Michael Tsai
(74) *Attorney, Agent, or Firm* — Dorsey & Whitney LLP

(57) ABSTRACT

An oral irrigator including a fluid reservoir, a pumping assembly, a pressure control assembly, and a nozzle. The pumping assembly comprises a power source, a motor in electrical communication with the power source, and a pump in fluid communication with the reservoir. The pressure control assembly is in fluid communication with the pump; mechanically varies a pressure of a fluid exiting the nozzle to change the outlet pressure of the oral irrigator a high pressure to a low pressure and vice versa.

11 Claims, 28 Drawing Sheets

(56) References Cited

U.S. PATENT DOCUMENTS

| | | | |
|---|---|---|---|
| 1,650,686 A | 11/1927 | Binks | |
| 1,669,889 A | 5/1928 | Andrews et al. | |
| 1,681,320 A | 8/1928 | Bergl et al. | |
| 1,933,454 A | 10/1933 | Sidney | |
| 2,107,686 A | 2/1938 | Bramsen et al. | |
| 2,230,238 A | 2/1941 | Duberstein et al. | |
| 2,417,759 A | 3/1947 | Johnson | |
| 2,669,233 A | 2/1954 | Friend | |
| 2,794,437 A | 6/1954 | Tash | |
| 2,783,919 A | 3/1957 | Ansell | |
| 2,870,932 A | 1/1959 | Davis | |
| 2,984,452 A | 5/1961 | Hooper | |
| 3,089,490 A | 5/1963 | Goldberg | |
| 3,096,913 A | 7/1963 | Jousson | |
| 3,144,867 A | 8/1964 | Trupp et al. | |
| 3,209,956 A | 10/1965 | McKenzie | |
| 3,216,619 A | 11/1965 | Richards et al. | |
| 3,225,759 A | 12/1965 | Drapen et al. | |
| 3,227,158 A | 1/1966 | Mattingly | |
| 3,266,623 A | 8/1966 | Poferl | |
| 3,297,558 A | 1/1967 | Hillquist | |
| D208,778 S | 10/1967 | Koch | |
| D209,204 S | 11/1967 | St. Clair et al. | |
| D209,395 S | 11/1967 | Gilbert | |
| D210,018 S | 1/1968 | Mattingly et al. | |
| D210,019 S | 1/1968 | Johnson et al. | |
| 3,370,214 A | 2/1968 | Aymar | |
| 3,391,696 A | 7/1968 | Woodward | |
| 3,393,673 A * | 7/1968 | Mattingly | A61C 1/0092 417/415 |
| 3,400,999 A | 9/1968 | Goldstein | |
| 3,418,552 A | 12/1968 | Holmes | |
| 3,420,228 A | 1/1969 | Kalbfeld | |
| 3,425,410 A | 2/1969 | Cammack | |
| 3,453,969 A | 7/1969 | Mattingly | |
| 3,465,751 A | 9/1969 | Powers | |
| 3,487,828 A | 1/1970 | Troy | |
| 3,489,268 A | 1/1970 | Meierhoefer | |
| 3,495,587 A | 2/1970 | Freedman | |
| 3,496,933 A | 2/1970 | Lloyd | |
| 3,499,440 A | 3/1970 | Gibbs | |
| 3,500,824 A | 3/1970 | Gilbert | |
| 3,501,203 A | 3/1970 | Falk | |
| 3,502,072 A | 3/1970 | Stillman | |
| 3,517,669 A | 6/1970 | Buono et al. | |
| D218,270 S | 8/1970 | Soper | |
| 3,522,801 A | 8/1970 | Robinson | |
| 3,532,221 A | 10/1970 | Kaluhiokalani et al. | |
| 3,536,065 A | 10/1970 | Moret | |
| 3,537,444 A | 11/1970 | Garn | |
| 3,538,950 A | 11/1970 | Porteners | |
| 3,547,110 A | 12/1970 | Balamuth | |
| 3,561,433 A | 2/1971 | Kovach | |
| D220,334 S | 3/1971 | Mackay et al. | |
| 3,570,525 A * | 3/1971 | Borsum | A61C 17/0202 137/320 |
| 3,572,375 A | 3/1971 | Rosenberg | |
| 3,578,884 A | 5/1971 | Jacobson | |
| 3,583,609 A | 6/1971 | Oppenheimer | |
| 3,590,813 A | 7/1971 | Roszyk | |
| 3,608,548 A | 9/1971 | Lewis | |
| D222,862 S | 1/1972 | Cook | |
| 3,636,947 A | 1/1972 | Balamuth | |
| 3,651,576 A | 3/1972 | Massa | |
| 3,669,101 A | 6/1972 | Kleiner | |
| 3,703,170 A | 11/1972 | Ryckman, Jr. | |
| 3,747,595 A | 7/1973 | Grossan | |
| 3,768,472 A | 10/1973 | Hodosh et al. | |
| 3,783,364 A | 1/1974 | Gallanis et al. | |
| 3,809,977 A | 5/1974 | Balamuth et al. | |
| 3,811,432 A * | 5/1974 | Moret | A61C 1/0092 601/161 |
| 3,820,532 A | 6/1974 | Eberhardt et al. | |
| 3,827,147 A | 8/1974 | Condon | |
| 3,840,795 A | 10/1974 | Roszyk et al. | |
| 3,847,145 A | 11/1974 | Grossan | |
| 3,854,209 A | 12/1974 | Franklin et al. | |
| 3,863,628 A | 2/1975 | Vit | |
| 3,874,506 A | 4/1975 | Hill et al. | |
| 3,881,868 A | 5/1975 | Duke | |
| 3,898,739 A | 8/1975 | Gayso | |
| 3,912,125 A | 10/1975 | Acklin | |
| 3,943,628 A | 3/1976 | Kronman et al. | |
| 3,973,558 A * | 8/1976 | Stouffer | A61C 17/02 128/DIG. 10 |
| 4,001,526 A | 1/1977 | Olson | |
| 4,004,302 A | 1/1977 | Hori | |
| 4,007,739 A | 2/1977 | Bron et al. | |
| 4,052,002 A | 10/1977 | Stouffer et al. | |
| D246,667 S | 12/1977 | Mackay et al. | |
| 4,060,870 A | 12/1977 | Cannarella | |
| 4,075,761 A | 2/1978 | Behne et al. | |
| 4,078,558 A | 3/1978 | Woog et al. | |
| 4,108,167 A | 8/1978 | Hickman et al. | |
| 4,108,178 A | 8/1978 | Betush | |
| 4,109,650 A | 8/1978 | Peclard | |
| 4,122,845 A | 10/1978 | Stouffer et al. | |
| 4,135,501 A | 1/1979 | Leunissan | |
| 4,141,352 A | 2/1979 | Ebner et al. | |
| 4,144,646 A | 3/1979 | Takemoto et al. | |
| 4,149,315 A | 4/1979 | Page, Jr. et al. | |
| 4,154,375 A | 5/1979 | Bippus | |
| 4,160,383 A | 7/1979 | Rauschenberger | |
| 4,182,038 A | 1/1980 | Fleer | |
| 4,201,200 A | 5/1980 | Hubner | |
| 4,215,476 A | 8/1980 | Armstrong | |
| 4,219,618 A | 8/1980 | Leonard | |
| 4,227,878 A | 10/1980 | Lohn | |
| 4,229,634 A | 10/1980 | Hickman et al. | |
| 4,236,889 A * | 12/1980 | Wright | A61C 17/02 433/86 |
| 4,248,589 A | 2/1981 | Lewis | |
| 4,249,899 A | 2/1981 | Davis | |
| 4,257,458 A | 3/1981 | Kondo et al. | |
| 4,262,799 A | 4/1981 | Perrett | |
| 4,266,934 A | 5/1981 | Pernot | |
| 4,276,023 A | 6/1981 | Phillips et al. | |
| 4,276,880 A | 7/1981 | Malmin | |
| 4,302,186 A | 11/1981 | Cammack et al. | |
| 4,303,064 A | 12/1981 | Buffa | |
| 4,303,070 A | 12/1981 | Ichikawa et al. | |
| 4,315,741 A | 2/1982 | Reichl | |
| 4,319,568 A | 3/1982 | Tregoning | |
| 4,331,422 A | 5/1982 | Heyman | |
| 4,337,040 A * | 6/1982 | Cammack | A61C 1/0092 433/80 |
| 4,340,365 A | 7/1982 | Pisanu | |
| 4,340,368 A | 7/1982 | Lococo | |
| D266,117 S | 9/1982 | Oberheim | |
| 4,353,694 A | 10/1982 | Pelerin | |
| 4,363,626 A | 12/1982 | Schmidt et al. | |
| 4,365,376 A | 12/1982 | Oda et al. | |
| 4,370,131 A | 1/1983 | Banko | |
| 4,374,354 A | 2/1983 | Petrovic et al. | |
| 4,382,167 A | 5/1983 | Maruyama et al. | |
| 4,382,786 A | 5/1983 | Lohn | |
| D270,000 S | 8/1983 | Ketler | |
| 4,412,823 A | 11/1983 | Sakai et al. | |
| 4,442,830 A | 4/1984 | Markau | |
| 4,442,831 A | 4/1984 | Trenary | |
| 4,452,238 A | 6/1984 | Kerr | |
| 4,454,866 A | 6/1984 | Fayen | |
| 4,512,769 A | 4/1985 | Kozam et al. | |
| 4,517,962 A | 5/1985 | Heckele | |
| 4,531,912 A | 7/1985 | Schuss et al. | |
| 4,531,913 A | 7/1985 | Taguchi | |
| 4,534,340 A | 8/1985 | Kerr et al. | |
| 4,552,130 A | 11/1985 | Kinoshita | |
| 4,561,214 A | 12/1985 | Inoue | |
| D283,374 S | 4/1986 | Cheuk-Yiu | |
| 4,585,415 A | 4/1986 | Hommann | |
| 4,591,777 A | 5/1986 | McCarty et al. | |
| 4,592,728 A | 6/1986 | Davis | |
| 4,602,906 A | 7/1986 | Grunenfelder | |

(56) References Cited

U.S. PATENT DOCUMENTS

| | | | |
|---|---|---|---|
| 4,607,627 A | 8/1986 | Leber et al. | |
| 4,613,074 A | 9/1986 | Schulze | |
| 4,619,612 A | 10/1986 | Weber et al. | |
| 4,629,425 A | 12/1986 | Detsch | |
| 4,636,198 A | 1/1987 | Stade | |
| 4,642,037 A | 2/1987 | Fritchman | |
| 4,644,937 A | 2/1987 | Hommann | |
| 4,645,488 A | 2/1987 | Matukas | |
| 4,647,831 A | 3/1987 | O'Malley et al. | |
| 4,648,838 A | 3/1987 | Schlachter | |
| 4,650,475 A | 3/1987 | Smith et al. | |
| 4,655,198 A | 4/1987 | Hommann | |
| 4,669,453 A | 6/1987 | Atkinson et al. | |
| 4,672,953 A | 6/1987 | DiVito | |
| 4,673,396 A | 6/1987 | Urbaniak | |
| D291,354 S | 8/1987 | Camens | |
| 4,716,352 A | 12/1987 | Hurn et al. | |
| 4,749,340 A | 6/1988 | Ikeda et al. | |
| 4,770,632 A | 9/1988 | Ryder et al. | |
| 4,783,321 A | 11/1988 | Spence | |
| 4,787,845 A | 11/1988 | Valentine | |
| 4,787,847 A | 11/1988 | Martin et al. | |
| 4,798,292 A | 1/1989 | Hauze | |
| 4,803,974 A | 2/1989 | Powell | |
| 4,804,364 A | 2/1989 | Dieras et al. | |
| 4,818,229 A | 4/1989 | Vasile | |
| 4,820,152 A | 4/1989 | Warrin et al. | |
| 4,821,923 A | 4/1989 | Skorka | |
| 4,824,368 A | 4/1989 | Hickman | |
| 4,826,431 A | 5/1989 | Fujimura et al. | |
| 4,832,683 A | 5/1989 | Idemoto et al. | |
| 4,854,869 A | 8/1989 | Lawhorn | |
| 4,861,340 A | 8/1989 | Smith et al. | |
| 4,862,876 A | 9/1989 | Lih-Sheng | |
| 4,869,720 A | 9/1989 | Chernack | |
| 4,880,382 A | 11/1989 | Moret et al. | |
| 4,886,452 A | 12/1989 | Lohn | |
| 4,900,252 A | 2/1990 | Liefke et al. | |
| 4,902,225 A | 2/1990 | Lohn | |
| 4,903,687 A | 2/1990 | Lih-Sheng | |
| 4,906,187 A | 3/1990 | Amadera | |
| 4,907,744 A | 3/1990 | Jousson | |
| 4,925,450 A | 5/1990 | Imonti et al. | |
| 4,928,675 A | 5/1990 | Thornton | |
| 4,930,660 A | 6/1990 | Porteous | |
| 4,941,459 A | 7/1990 | Mathur | |
| 4,950,159 A | 8/1990 | Hansen | |
| 4,958,629 A | 9/1990 | Peace et al. | |
| 4,958,751 A | 9/1990 | Curtis et al. | |
| 4,959,199 A | 9/1990 | Brewer | |
| 4,961,698 A | 10/1990 | Vlock | |
| 4,966,551 A | 10/1990 | Betush | |
| 4,969,874 A | 11/1990 | Michel et al. | |
| 4,973,247 A | 11/1990 | Varnes et al. | |
| 4,973,250 A | 11/1990 | Milman | |
| 4,975,054 A | 12/1990 | Esrock | |
| 4,979,503 A | 12/1990 | Chernack | |
| 4,979,504 A | 12/1990 | Mills | |
| 4,989,590 A | 2/1991 | Baum et al. | |
| 4,998,880 A | 3/1991 | Nerli | |
| 5,013,241 A | 5/1991 | Von Gutfeld et al. | |
| 5,014,884 A | 5/1991 | Wunsch | |
| 5,019,054 A | 5/1991 | Clement et al. | |
| 5,027,798 A | 7/1991 | Primiano | |
| 5,029,576 A | 7/1991 | Evans, Sr. | |
| 5,033,617 A | 7/1991 | Hartwein et al. | |
| 5,033,961 A | 7/1991 | Kankler et al. | |
| D318,918 S | 8/1991 | Hartwein | |
| 5,046,486 A | 9/1991 | Grulke et al. | |
| 5,049,071 A | 9/1991 | Davis et al. | |
| 5,060,825 A | 10/1991 | Palmer et al. | |
| 5,061,180 A * | 10/1991 | Wiele | A61C 17/0208 433/91 |
| 5,062,795 A | 11/1991 | Woog | |
| 5,064,168 A | 11/1991 | Raines et al. | |
| D322,314 S | 12/1991 | Ohbayashi | |
| 5,071,346 A | 12/1991 | Domaas | |
| 5,082,115 A | 1/1992 | Hutcheson | |
| 5,082,443 A | 1/1992 | Lohn | |
| 5,085,317 A | 2/1992 | Jensen et al. | |
| 5,086,756 A | 2/1992 | Powell | |
| 5,095,893 A | 3/1992 | Rawden, Jr. | |
| 5,098,291 A | 3/1992 | Curtis et al. | |
| 5,098,676 A | 3/1992 | Brooks, Jr. | |
| 5,100,319 A | 3/1992 | Baum | |
| 5,117,871 A | 6/1992 | Gardner et al. | |
| 5,125,835 A | 6/1992 | Young | |
| 5,127,831 A | 7/1992 | Bab | |
| 5,142,723 A | 9/1992 | Lustig et al. | |
| 5,150,841 A | 9/1992 | Silvenis et al. | |
| 5,172,810 A | 12/1992 | Brewer | |
| 5,173,273 A | 12/1992 | Brewer | |
| 5,183,035 A | 2/1993 | Weir | |
| 5,197,458 A | 3/1993 | Ito et al. | |
| 5,197,460 A | 3/1993 | Ito et al. | |
| 5,199,871 A | 4/1993 | Young | |
| 5,203,697 A | 4/1993 | Malmin | |
| 5,203,769 A | 4/1993 | Clement et al. | |
| 5,204,004 A | 4/1993 | Johnston et al. | |
| 5,208,933 A | 5/1993 | Lustig et al. | |
| 5,215,193 A | 6/1993 | Dennis | |
| 5,218,956 A | 6/1993 | Handler et al. | |
| 5,220,914 A * | 6/1993 | Thompson | A61C 17/0214 601/155 |
| 5,228,646 A | 7/1993 | Raines | |
| 5,230,624 A | 7/1993 | Wolf et al. | |
| 5,232,687 A | 8/1993 | Geimer | |
| 5,235,968 A | 8/1993 | Woog | |
| 5,241,714 A | 9/1993 | Barry | |
| 5,246,367 A | 9/1993 | Ito et al. | |
| 5,252,064 A | 10/1993 | Baum et al. | |
| D341,200 S | 11/1993 | Yoshimoto | |
| 5,257,933 A | 11/1993 | Jousson | |
| 5,261,448 A | 11/1993 | Furuya et al. | |
| D341,943 S | 12/1993 | Si-Hoe | |
| 5,267,586 A | 12/1993 | Jankavaara | |
| 5,269,684 A | 12/1993 | Fischer | |
| 5,281,137 A | 1/1994 | Jousson | |
| 5,281,139 A | 1/1994 | Frank et al. | |
| 5,282,745 A | 2/1994 | Wiltrout et al. | |
| 5,286,192 A | 2/1994 | Dixon | |
| 5,286,201 A | 2/1994 | Yu | |
| 5,297,962 A | 3/1994 | O'Connor et al. | |
| D346,212 S | 4/1994 | Hosl | |
| 5,302,123 A | 4/1994 | Bechard | |
| 5,317,691 A | 5/1994 | Traeger | |
| 5,321,865 A | 6/1994 | Kaeser | |
| 5,331,704 A | 7/1994 | Rosen et al. | |
| 5,344,317 A | 9/1994 | Pacher et al. | |
| 5,346,677 A | 9/1994 | Risk | |
| D351,892 S | 10/1994 | Wolf et al. | |
| 5,360,338 A | 11/1994 | Waggoner | |
| 5,368,548 A | 11/1994 | Jousson | |
| 5,370,534 A | 12/1994 | Wolf et al. | |
| D354,168 S | 1/1995 | Hartwein | |
| 5,378,149 A | 1/1995 | Stropko | |
| 5,380,201 A | 1/1995 | Kawata | |
| D356,864 S | 3/1995 | Woog | |
| 5,399,089 A | 3/1995 | Eichman et al. | |
| D358,883 S | 5/1995 | Vos | |
| 5,456,672 A | 10/1995 | Diederich et al. | |
| 5,465,445 A | 11/1995 | Yeh | |
| 5,467,495 A | 11/1995 | Boland et al. | |
| 5,468,148 A | 11/1995 | Ricks | |
| 5,470,305 A | 11/1995 | Arnett et al. | |
| 5,474,450 A | 12/1995 | Chronister | |
| 5,474,451 A | 12/1995 | Dalrymple et al. | |
| 5,476,379 A | 12/1995 | Disel | |
| 5,484,281 A | 1/1996 | Renow et al. | |
| 5,487,877 A | 1/1996 | Choi | |
| 5,490,779 A | 2/1996 | Malmin | |
| 5,505,916 A | 4/1996 | Berry, Jr. | |
| D369,656 S | 5/1996 | Vos | |
| 5,525,058 A | 6/1996 | Gallant et al. | |

(56) References Cited

U.S. PATENT DOCUMENTS

| | | |
|---|---|---|
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,025 A | 9/1996 | Kinsel |
| 5,556,001 A * | 9/1996 | Weissman .......... A61C 17/0202 222/1 |
| 5,564,629 A * | 10/1996 | Weissman ................. B05B 7/28 239/310 |
| D377,091 S | 12/1996 | Scott, Sr. |
| 5,616,028 A | 4/1997 | Hafele et al. |
| 5,622,501 A | 4/1997 | Levy |
| 5,634,791 A | 6/1997 | Matsuura et al. |
| 5,636,987 A | 6/1997 | Serfaty |
| 5,640,735 A | 6/1997 | Manning |
| 5,653,591 A | 8/1997 | Loge |
| 5,659,995 A | 8/1997 | Hoffman |
| 5,667,483 A | 9/1997 | Santos |
| D386,576 S | 11/1997 | Wang et al. |
| 5,683,192 A | 11/1997 | Kilfoil |
| 5,685,829 A | 11/1997 | Allen |
| 5,685,851 A | 11/1997 | Murphy et al. |
| 5,697,784 A | 12/1997 | Hafele et al. |
| D388,612 S | 1/1998 | Stutzer et al. |
| D388,613 S | 1/1998 | Stutzer et al. |
| 5,709,545 A | 1/1998 | Johnston et al. |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,654 A | 7/1998 | Foley et al. |
| 5,795,153 A | 8/1998 | Rechmann |
| 5,796,325 A | 8/1998 | Lundell et al. |
| 5,833,065 A | 11/1998 | Burgess |
| 5,836,030 A | 11/1998 | Hazeu et al. |
| D402,744 S | 12/1998 | Zuege |
| 5,851,079 A | 12/1998 | Horstman et al. |
| D403,511 S | 1/1999 | Serbinski |
| D406,334 S | 3/1999 | Rosenthal et al. |
| 5,876,201 A | 3/1999 | Wilson et al. |
| D408,511 S | 4/1999 | Allen et al. |
| 5,901,397 A | 5/1999 | Häfele et al. |
| 5,934,902 A | 8/1999 | Abahusayn |
| D413,975 S | 9/1999 | Maeda |
| D417,082 S | 11/1999 | Classen et al. |
| 5,993,402 A | 11/1999 | Sauer et al. |
| 6,030,215 A | 2/2000 | Ellion et al. |
| 6,038,960 A | 3/2000 | Fukushima et al. |
| 6,039,180 A | 3/2000 | Grant |
| D425,615 S | 5/2000 | Bachman et al. |
| D425,981 S | 5/2000 | Bachman et al. |
| 6,056,710 A | 5/2000 | Bachman et al. |
| D426,633 S | 6/2000 | Bachman et al. |
| 6,089,865 A | 7/2000 | Edgar |
| 6,116,866 A | 9/2000 | Tomita et al. |
| 6,124,699 A | 9/2000 | Suzuki et al. |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| D437,049 S | 1/2001 | Hartwein |
| 6,193,512 B1 | 2/2001 | Wallace |
| 6,193,932 B1 | 2/2001 | Wu et al. |
| 6,199,239 B1 | 3/2001 | Dickerson |
| 6,200,134 B1 | 3/2001 | Kovac |
| D439,781 S | 4/2001 | Spore |
| 6,217,835 B1 | 4/2001 | Riley et al. |
| D441,861 S | 5/2001 | Hafliger |
| 6,233,773 B1 | 5/2001 | Karge et al. |
| 6,234,205 B1 | 5/2001 | D'Amelio et al. |
| 6,237,178 B1 | 5/2001 | Krammer et al. |
| 6,247,929 B1 | 6/2001 | Bachman et al. |
| D448,236 S | 9/2001 | Murray |
| 6,293,792 B1 | 9/2001 | Hanson |
| D449,884 S | 10/2001 | Tobin et al. |
| 6,343,174 B1 | 1/2002 | Neuberger |
| D453,453 S | 2/2002 | Lun |
| 6,363,565 B1 | 4/2002 | Paffrath |
| D464,799 S | 10/2002 | Crossman et al. |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,375 B1 | 12/2002 | Srinath et al. |
| 6,497,572 B2 | 12/2002 | Hood et al. |
| 6,502,584 B1 | 1/2003 | Fordham |
| D470,660 S | 2/2003 | Schaber |
| 6,558,344 B2 | 5/2003 | McKinnon et al. |
| 6,561,808 B2 | 5/2003 | Neuberger et al. |
| D475,346 S | 6/2003 | McCurrach et al. |
| 6,589,477 B1 | 7/2003 | Frieze et al. |
| 6,602,071 B1 | 8/2003 | Ellion et al. |
| 6,632,091 B1 | 10/2003 | Cise et al. |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,663,386 B1 | 12/2003 | Moelsgaard |
| 6,669,059 B2 | 12/2003 | Mehta |
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| 7,367,803 B2 | 5/2008 | Egeresi |
| D574,952 S | 8/2008 | Boyd et al. |
| D577,198 S | 9/2008 | Jimenez |
| 7,455,521 B2 | 11/2008 | Fishburne, Jr. |
| 7,469,440 B2 | 12/2008 | Boland et al. |
| 7,500,584 B2 | 3/2009 | Schutz |
| D590,492 S | 4/2009 | Powell |
| 7,670,141 B2 | 3/2010 | Thomas et al. |
| 7,677,888 B1 | 3/2010 | Halm |
| 7,878,403 B2 | 2/2011 | Hennick et al. |
| 8,403,665 B2 | 3/2013 | Thomas et al. |
| 8,408,483 B2 | 4/2013 | Boyd et al. |

(56) References Cited

U.S. PATENT DOCUMENTS

| | | | |
|---|---|---|---|
| 9,050,157 B2 | 6/2015 | Boyd et al. | |
| 2002/0090252 A1 | 7/2002 | Hall et al. | |
| 2002/0119415 A1 | 8/2002 | Bailey | |
| 2002/0182186 A1 | 12/2002 | Loeb | |
| 2003/0098249 A1 | 5/2003 | Rollock | |
| 2003/0204155 A1 | 10/2003 | Egeresi | |
| 2003/0213075 A1 | 11/2003 | Hui et al. | |
| 2004/0045107 A1 | 3/2004 | Egeresi | |
| 2004/0076921 A1 | 4/2004 | Gofman et al. | |
| 2004/0122377 A1 | 6/2004 | Fischer et al. | |
| 2004/0126730 A1 | 7/2004 | Panagotacos | |
| 2004/0209222 A1* | 10/2004 | Snyder | A61C 17/02 433/80 |
| 2005/0049620 A1 | 3/2005 | Chang | |
| 2005/0064371 A1 | 3/2005 | Soukos et al. | |
| 2005/0101894 A1 | 5/2005 | Hippensteel | |
| 2005/0177079 A1 | 8/2005 | Pan | |
| 2005/0271531 A1 | 12/2005 | Brown et al. | |
| 2006/0008373 A1 | 1/2006 | Schutz | |
| 2006/0021165 A1 | 2/2006 | Boland et al. | |
| 2006/0026784 A1 | 2/2006 | Moskovich et al. | |
| 2006/0057539 A1 | 3/2006 | Sodo | |
| 2006/0078844 A1 | 4/2006 | Goldman et al. | |
| 2006/0079818 A1 | 4/2006 | Yande | |
| 2007/0082316 A1 | 4/2007 | Zhadanov et al. | |
| 2007/0113360 A1 | 5/2007 | Tsai | |
| 2007/0202459 A1 | 8/2007 | Boyd et al. | |
| 2007/0203439 A1 | 8/2007 | Boyd et al. | |
| 2007/0254260 A1 | 11/2007 | Alden | |
| 2008/0008979 A1 | 1/2008 | Thomas et al. | |
| 2010/0010524 A1* | 1/2010 | Barrington | A61B 17/3203 606/167 |
| 2010/0261134 A1 | 10/2010 | Boyd et al. | |
| 2010/0261137 A1 | 10/2010 | Boyd et al. | |
| 2010/0330527 A1 | 12/2010 | Boyd et al. | |
| 2011/0097683 A1 | 4/2011 | Boyd et al. | |
| 2011/0139826 A1 | 6/2011 | Hair et al. | |
| 2012/0064480 A1 | 3/2012 | Hegemann | |
| 2012/0141952 A1 | 6/2012 | Snyder et al. | |
| 2014/0193774 A1 | 7/2014 | Snyder et al. | |

FOREIGN PATENT DOCUMENTS

| | | |
|---|---|---|
| CH | 655237 | 4/1987 |
| DE | 1466963 | 5/1969 |
| DE | 2409752 | 9/1975 |
| DE | 2545936 | 4/1977 |
| DE | 2910982 | 2/1980 |
| EP | 0023672 | 7/1980 |
| EP | 0515983 A1 | 12/1992 |
| FR | 2556954 | 6/1985 |
| FR | 2654627 | 5/1991 |
| GB | 1182031 | 2/1970 |
| GB | 2018605 | 10/1979 |
| JP | 2-134150 | 4/1990 |
| WO | WO95/16404 | 6/1995 |
| WO | 01/10327 A1 | 2/2001 |
| WO | WO2004/021958 | 3/2004 |
| WO | WO2004/039205 | 5/2004 |
| WO | 2004060259 A2 | 7/2004 |
| WO | 2008157585 A1 | 12/2008 |
| WO | 2013124691 A1 | 8/2013 |

OTHER PUBLICATIONS

The Right Tool, Electron Fusion Devices, Inc., 2 pages, at least as early as Feb. 1991.
Japanese Packaging, 2 pages, at least as early as Dec. 2002.
Japanese Instruction Brochure, 20 pages, at least as early as Dec. 2002.
Brochure: Woog International, "You have a 98% chance of getting gum disease. Unless you read this.", Lancaster, Pennsylvania, 5 pages, Feb. 1987.
Brochure: Woog International, "We put the control of home dental care back into the hands of the professional", Lancaster, Pennsylvania, 2 pages, Feb. 1987.
Brochure: WOOG International, "Products at a Glance: Home Dental Care System" WOOG ORAJET, 3 pages, at least as early as Dec. 18, 1998.
Website: http://www.just4teeth.com/product/Panasonic/Panasonic_Portable_Irrigator.htm, 2 pages, at least as early as Jun. 20, 2003.
Website: http://www.videodirectstore.com/store/merchant.mv?Screen=PROD&Product_Code=EW1' . . . , 2 pages, at least as early as Jun. 20, 2003.
Website: http://products.consumerguide.com/cp/family/review/index.cfm/id/18742, 2 pages, at least as early as Jun. 20, 2003.
Website: http://www.racekarteng.com/images/walbroparts.gif and http://www.muller.net/mullermachine/docs/walbro1.html, 4 pages, at least as early as Jun. 20, 2003.

* cited by examiner

ORAL IRRIGATOR WITH VARIABLE PRESSURE

CROSS-REFERENCE TO RELATED APPLICATIONS

The present application is a continuation patent application of U.S. patent application Ser. No. 13/566,652, filed Aug. 3, 2012 entitled "Oral Irrigator with Hand Conforming Housing," which is a continuation patent application of U.S. Pat. No. 8,403,665, filed Feb. 22, 2010 entitled "Oral Irrigator," which is a continuation patent application of U.S. Pat. No. 7,670,141, filed Jul. 7, 2006 entitled "Oral Irrigator," the disclosures of which are hereby incorporated herein in their entireties.

TECHNICAL FIELD

The present invention relates to health and personal hygiene equipment and methods of controlling such equipment. More particularly, the present invention relates to oral irrigators and methods of controlling such equipment.

BACKGROUND

Oral irrigators for discharging a high-pressure fluid stream into a user's oral cavity are well known in the art and are useful for promoting oral hygiene and health. For example, a particularly effective oral irrigator is disclosed in U.S. patent application Ser. No. 10/749,675 which is hereby incorporated by reference in its entirety into the present application.

It is advantageous for an oral irrigator to discharge a fluid stream at a select pulse rate that is generally constant. For example, a particularly useful constant pulse rate is 1200 cycles per minute.

Depending on the user and the part of the oral cavity being impacted by the fluid stream, a high-pressure fluid stream or a low-pressure fluid stream may be preferred. Thus, it is preferable to offer oral irrigators with an ability to vary the pressure of the fluid stream discharging from the oral irrigator. Prior art oral irrigators have attempted to meet this need by adjusting pumping speed. Unfortunately, this approach results in an inability of the oral irrigator to provide a generally constant pulse rate.

SUMMARY

A handheld oral irrigator general includes a fluid reservoir, a pump, a pressure control assembly, and a nozzle. In an implementation disclosed herein, the pump may include a suction side and a discharge side. The suction side is in fluid communication with the fluid reservoir. The pressure control assembly may include a casing and a member displaceable within the casing. The casing has an inlet and an outlet. The inlet is in fluid communication with the discharge side of the pump, and the nozzle is in fluid communication with the outlet of the casing. In one embodiment, the member is longitudinally displaceable within the casing.

In some embodiments, the oral irrigator may also include an actuator for displacing the member within the casing. The member may have a portion that extends through the casing to couple to the actuator. In one embodiment, the portion of the member is an arm that extends through a longitudinally extending slot in the casing. A fluid flow path may extend from the inlet to the outlet and may be modifiable between a first route that extends along at least a portion of the member and a second route that does not.

In another implementation, an oral irrigator may have a pump, a discharge nozzle and a pressure control. The pump may have a generally constant operating speed and feeds the discharge nozzle. The pressure control may be adapted to modify a discharge pressure at the nozzle without a significant change in pump speed. The pressure control modifies a level of fluid flow restriction between the pump and the nozzle. The pressure control may modify the diameter of a fluid flow path extending through the pressure control. The pressure control may also modify the length of a fluid flow path extending through the pressure control. The pressure control may also modify the number of direction changes of a fluid flow path extending through the pressure control.

In a further implementation, an oral irrigator has a pump and a pressure adjustment assembly. The pump supplies a nozzle. The pressure adjustment assembly may be configured to provide a first fluid flow path associated with a high nozzle discharge pressure and a second fluid flow path associated with a low nozzle discharge pressure. The pressure adjustment assembly may be located between the pump and nozzle.

In one embodiment, the first fluid flow path offers a more direct route to the nozzle than the second fluid flow path. In another embodiment, the first fluid flow path has a length that is shorter than a length of the second fluid flow path. In a further embodiment, the second fluid flow path has a diameter that is smaller than a diameter of the first fluid flow path.

The pressure adjustment assembly may have a casing and a member displaceable within the casing. The casing defines a first orifice and the member a second orifice. The second fluid flow path extends through both orifices. The first fluid flow path extends only through the orifice of the casing.

In one embodiment, the pressure adjustment assembly may have a casing and a member displaceable within the casing. A portion of the second fluid flow path extends circumferentially about at least a portion of the member. The member may be generally cylindrical and define a groove extending about at least a portion of the circumferential outer surface of the member. The casing may define an inlet orifice that aligns with the groove to form a portion of the second fluid flow path. The member may also have a longitudinally extending center lumen in fluid contact with the groove via an orifice extending through a wall of the member.

In another implementation an oral irrigator may have a pump and a pressure adjustment assembly. The pump supplies a nozzle. The pressure adjustment assembly may have a first fluid flow friction setting associated with a high nozzle discharge pressure and a second fluid flow friction setting associated with a low nozzle discharge pressure.

In a further implementation, a method of controlling a nozzle discharge pressure of an oral irrigator having a pump that feeds a nozzle is described. The method includes modifying a fluid flow friction value of a fluid flow path between the pump and nozzle by modifying the fluid flow path. The fluid flow path may be modified by one or more of the following actions: changing its length, changing its diameter or by changing its number of direction deviations.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION OF THE INVENTION

In one embodiment, a handheld oral irrigator 10 allows a user to adjust the discharge pressure of the irrigator generated fluid stream while maintaining the pulse rate of the fluid stream. Thus, the handheld oral irrigator 10 is advantageous over the prior art because it allows a user to adjust the fluid stream discharge pressure to suit the user's comfort preference, while still allowing the oral irrigator to supply the fluid stream at a preferred or most effective pulse rate (e.g., 1200 cycles per minute).

Figure 1:
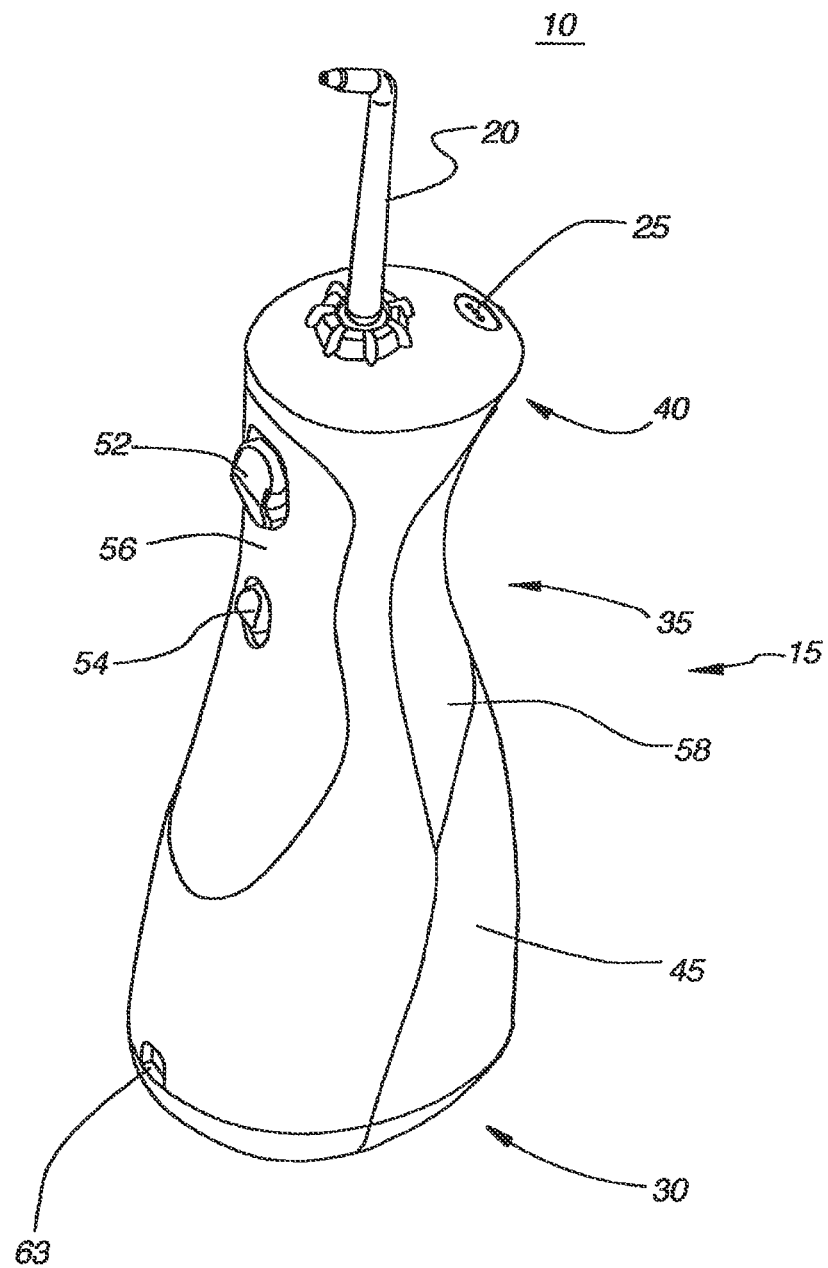
FIG. 1 is a top isometric view of the handheld oral irrigator.
Figure 2:
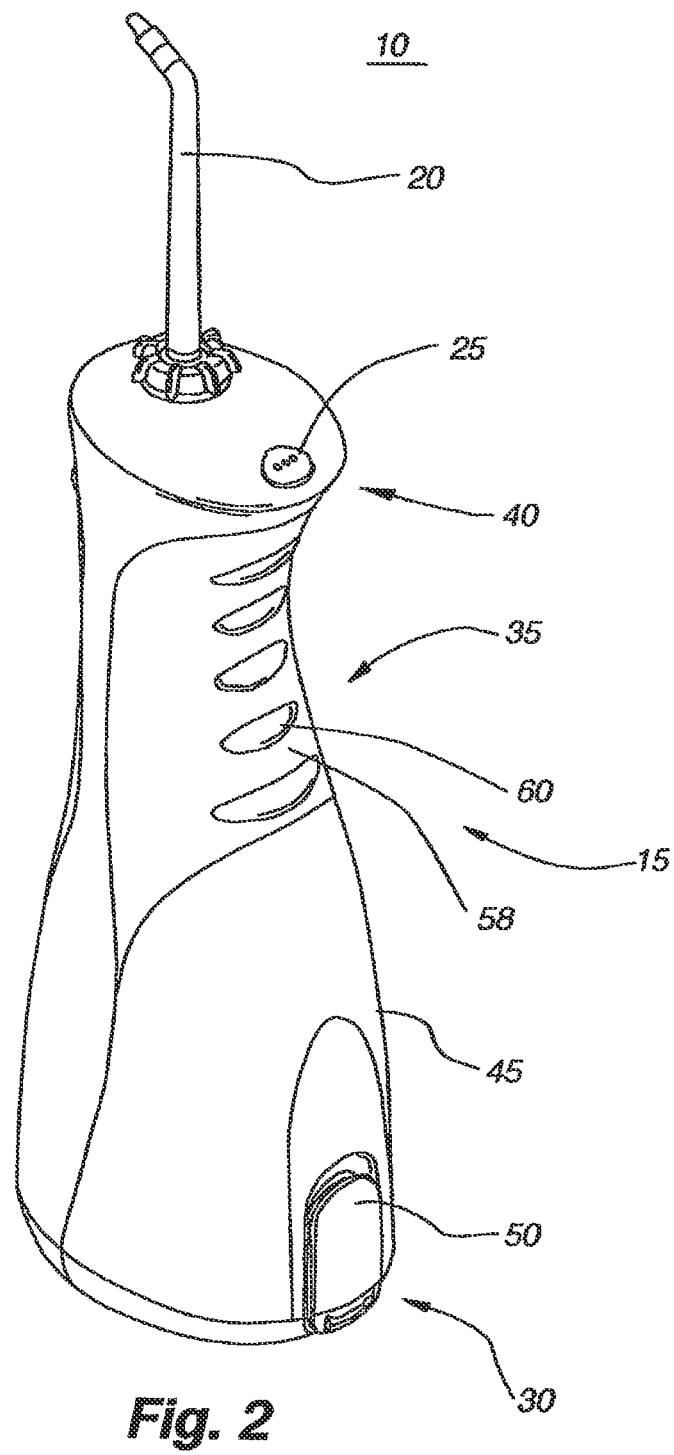
FIG. 2 is a top isometric view of the handheld oral irrigator.
Figure 3:
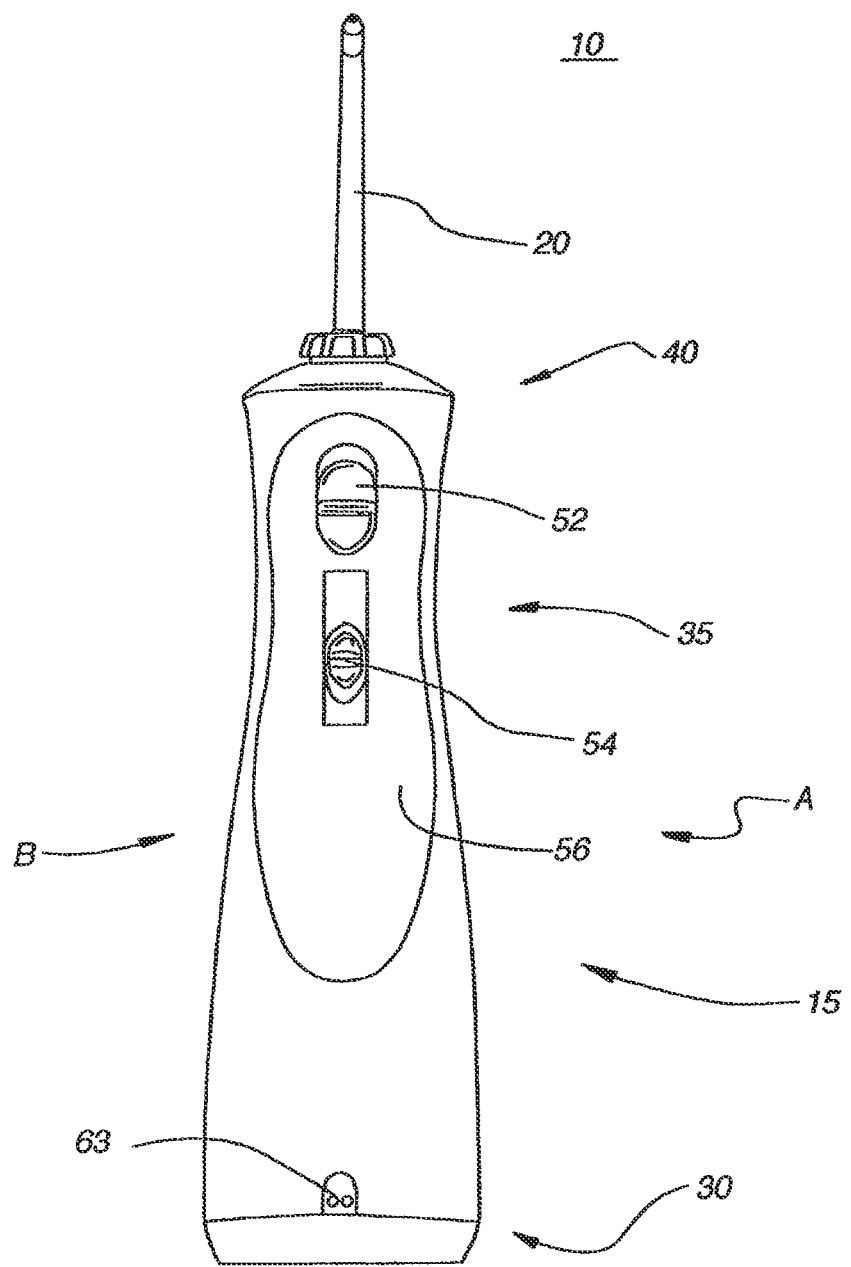
FIG. 3 is a control side elevation of the handheld oral irrigator.
Figure 4:
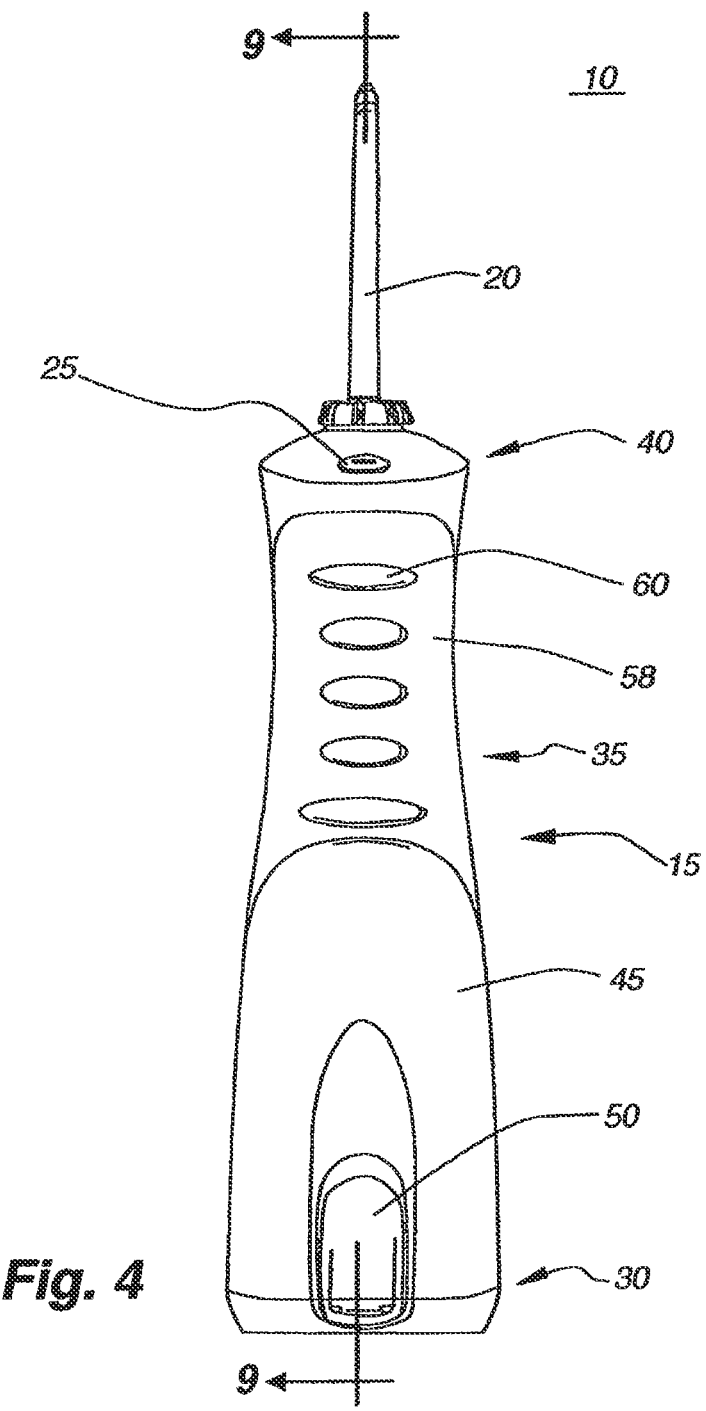
FIG. 4 is a reservoir side elevation of the handheld oral irrigator.
Figure 5:
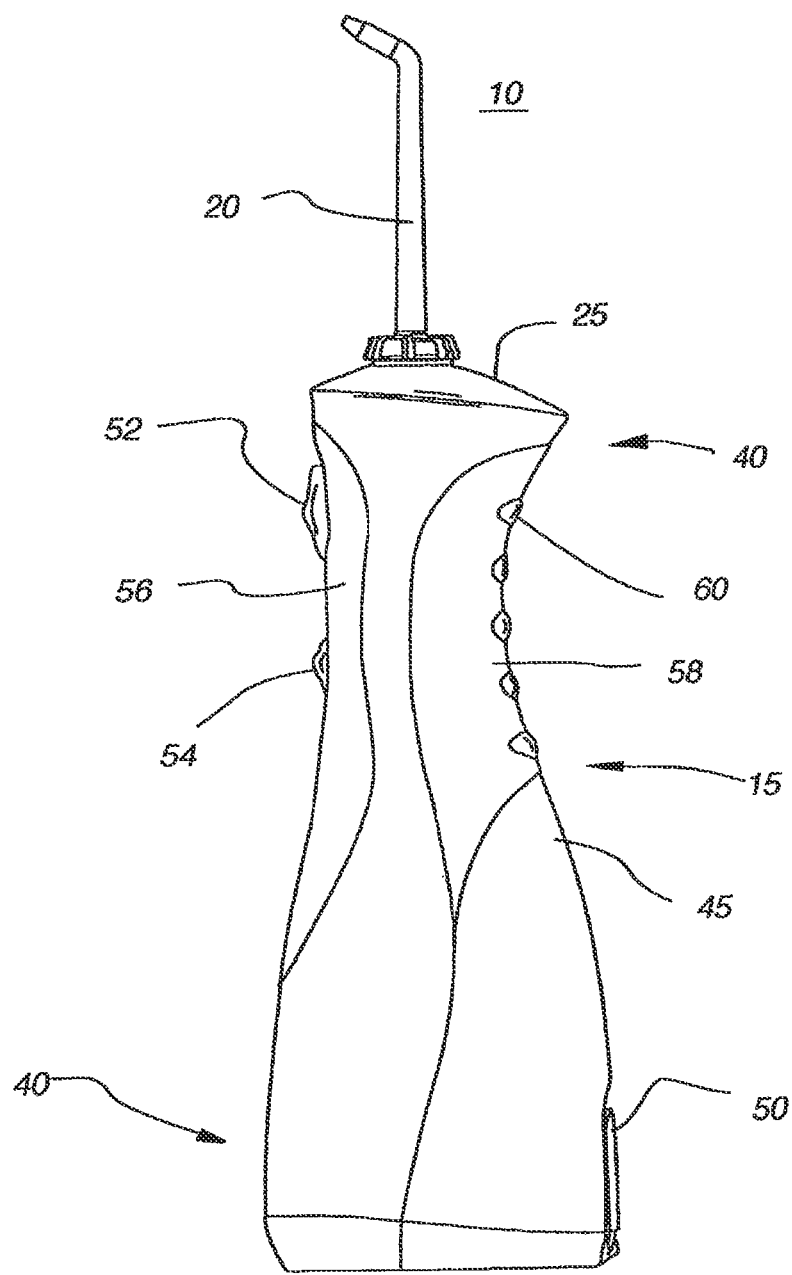
FIG. 5 is a right side elevation of the handheld oral irrigator as if viewed from the direction of arrow A in FIG. 3.
Figure 6:
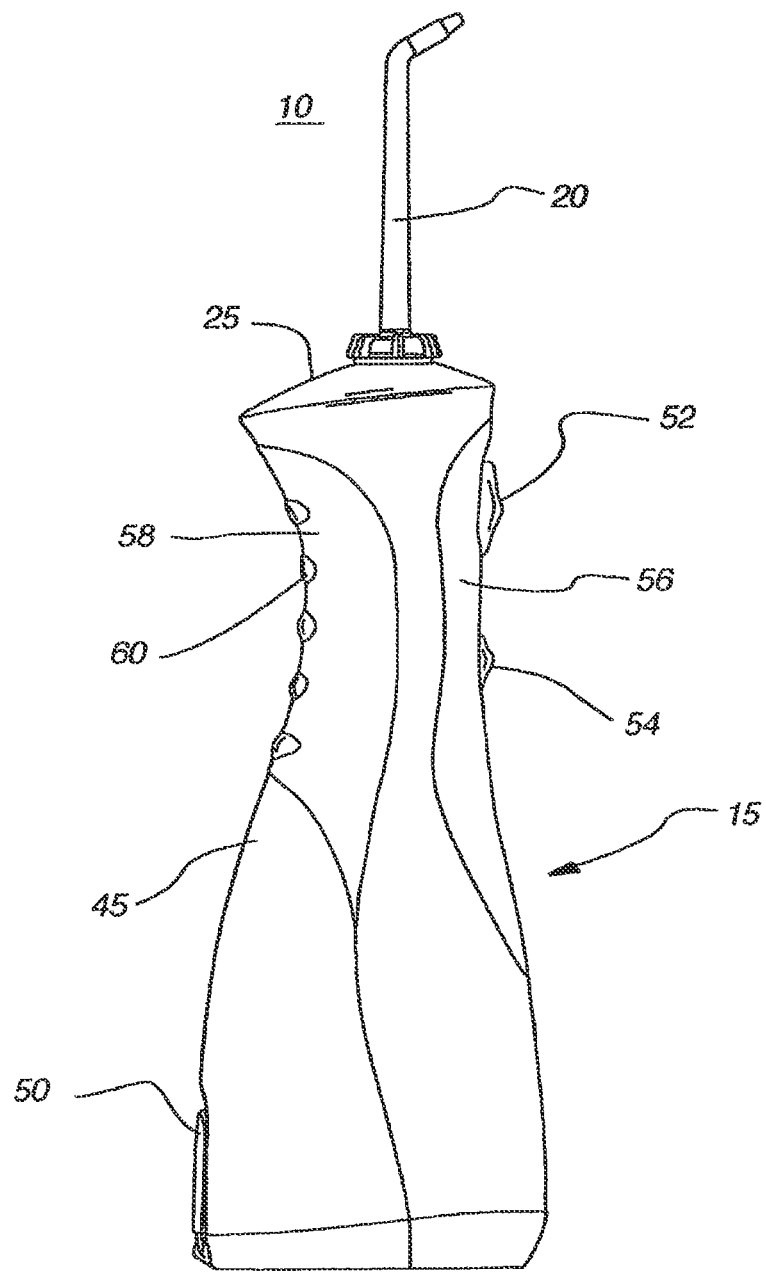
FIG. 6 is a left side elevation of the handheld oral irrigator as if viewed from the direction of arrow B in FIG. 3.
Figure 7:
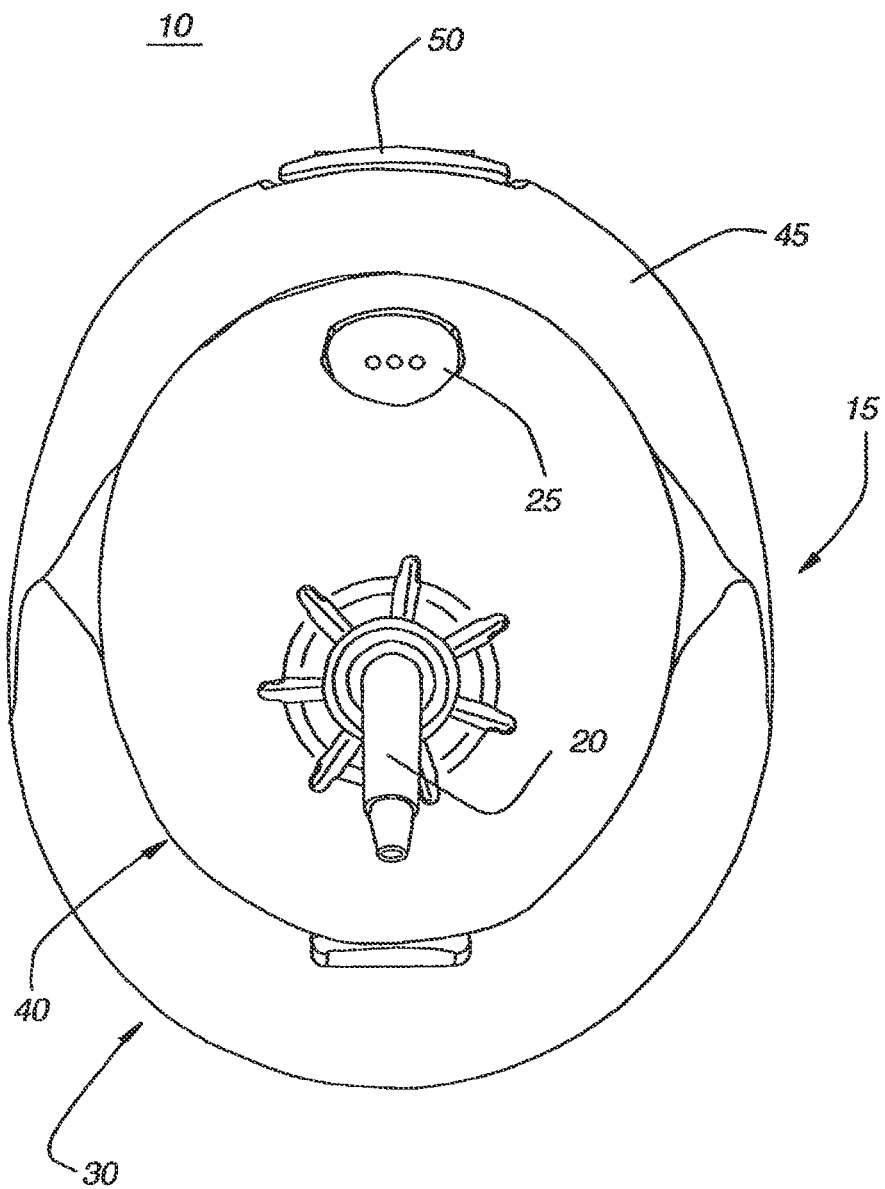
FIG. 7 is a top plan view of the handheld oral irrigator.
Figure 8:
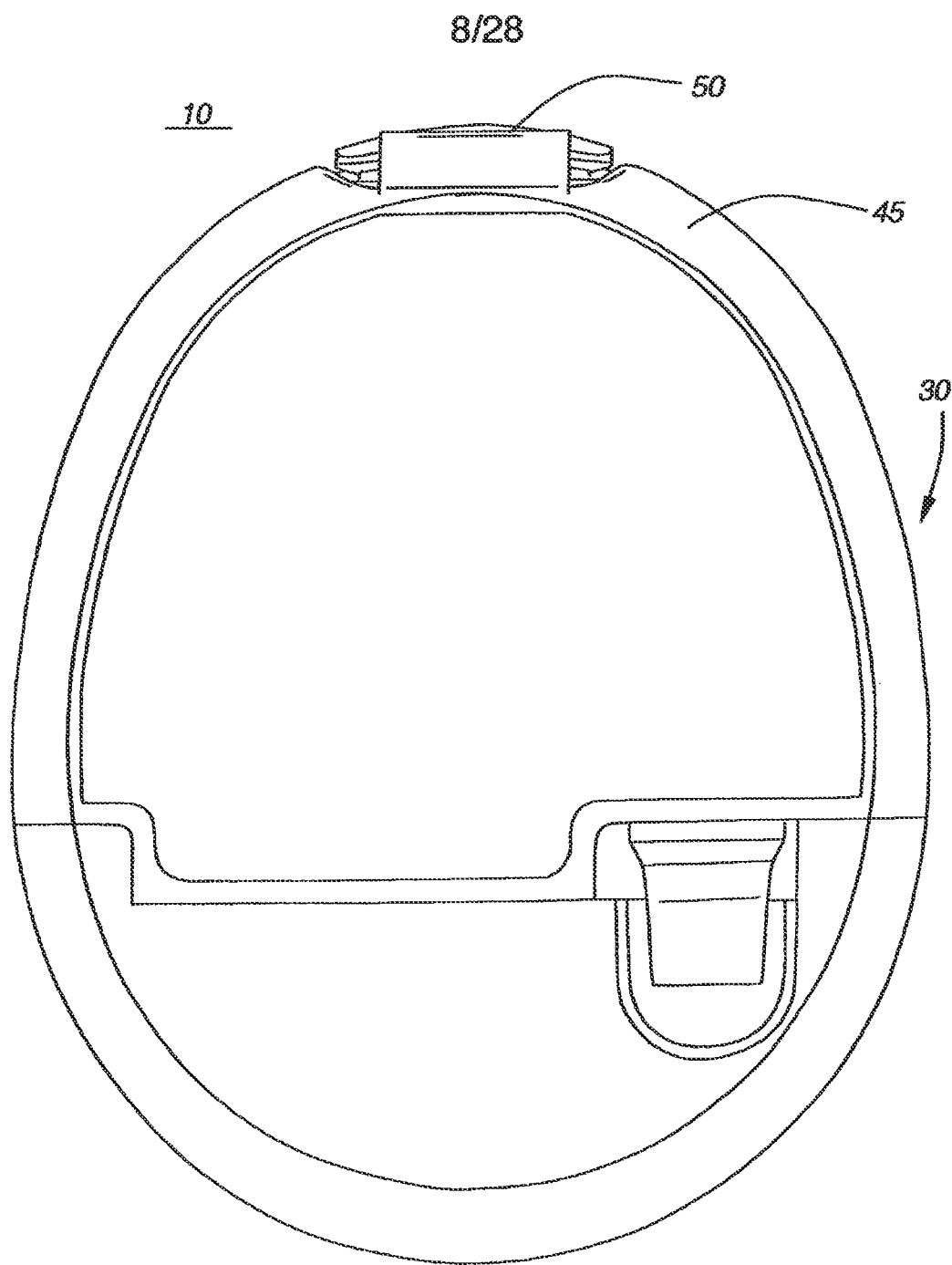
FIG. 8 is a bottom plan view of the handheld oral irrigator.

For a discussion of the overall external configuration of one embodiment of the handheld oral irrigator 10, reference is made to FIGS. 1-8. FIGS. 1 and 2 are top isometric views of the handheld oral irrigator 10. FIG. 3 is a control side elevation of the handheld oral irrigator 10. FIG. 4 is a reservoir side elevation of the handheld oral irrigator 10. FIG. 5 is a right side elevation of the handheld oral irrigator 10 as if viewed from the direction of arrow A in FIG. 3. FIG. 6 is a left side elevation of the handheld oral irrigator 10 as if viewed from the direction of arrow B in FIG. 3. FIG. 7 is a top plan view of the handheld oral irrigator 10. FIG. 8 is a bottom plan view of the handheld oral irrigator 10.

As shown in FIGS. 1-7, in one embodiment, the irrigator 10 includes a handle portion 15 and a nozzle 20 with an orthodontic tip at its distal end. The nozzle 20 extends from a top end of the handle portion 15. The nozzle 20 is detachable from the handle portion 15 via a nozzle release button 25 located on the top of the handle portion 15.

As illustrated in FIGS. 1-6, in one embodiment, the handle portion 15 has a modified hourglass shape that gradually narrows from a wide base 30 (the proximal end of the irrigator 10) to a narrow gripping area 35 and gradually widens from the narrow gripping area 35 to a moderately wide top 40 (the distal end of the irrigator 10). The hourglass shape is aesthetically pleasing and ergonomically shaped to accommodate a user's hand, which in one embodiment will be a child or adolescent hand.

As indicated in FIGS. 1, 2 and 4-8, in one embodiment, the handle portion 15 includes a reservoir 45 that forms a part of the base 30. The reservoir 45 is removable from the rest of the handle portion 15 and includes a fill port 50 near the bottom of the reservoir 45. To fill the reservoir with fluid, the reservoir 45 may be disengaged and removed from the rest of the handle portion 15, the cap of the fill port 50 is opened, and a fluid is flowed into the reservoir 45 via the open fill port 50. Once the reservoir 45 is filled, the cap is closed on the fill port 50 and the reservoir 45 is reattached to the rest of the handle portion 15.

As can be understood from FIGS. 1, 2 and 4-8, the reservoir 45 may be filled while still attached to the rest of the handle portion 15. To do this, the cap of the fill port 50 is opened and a fluid is flowed into the reservoir 45 via the open fill port 50. Once the reservoir 45 is filled, the cap is closed.

Figure 25:
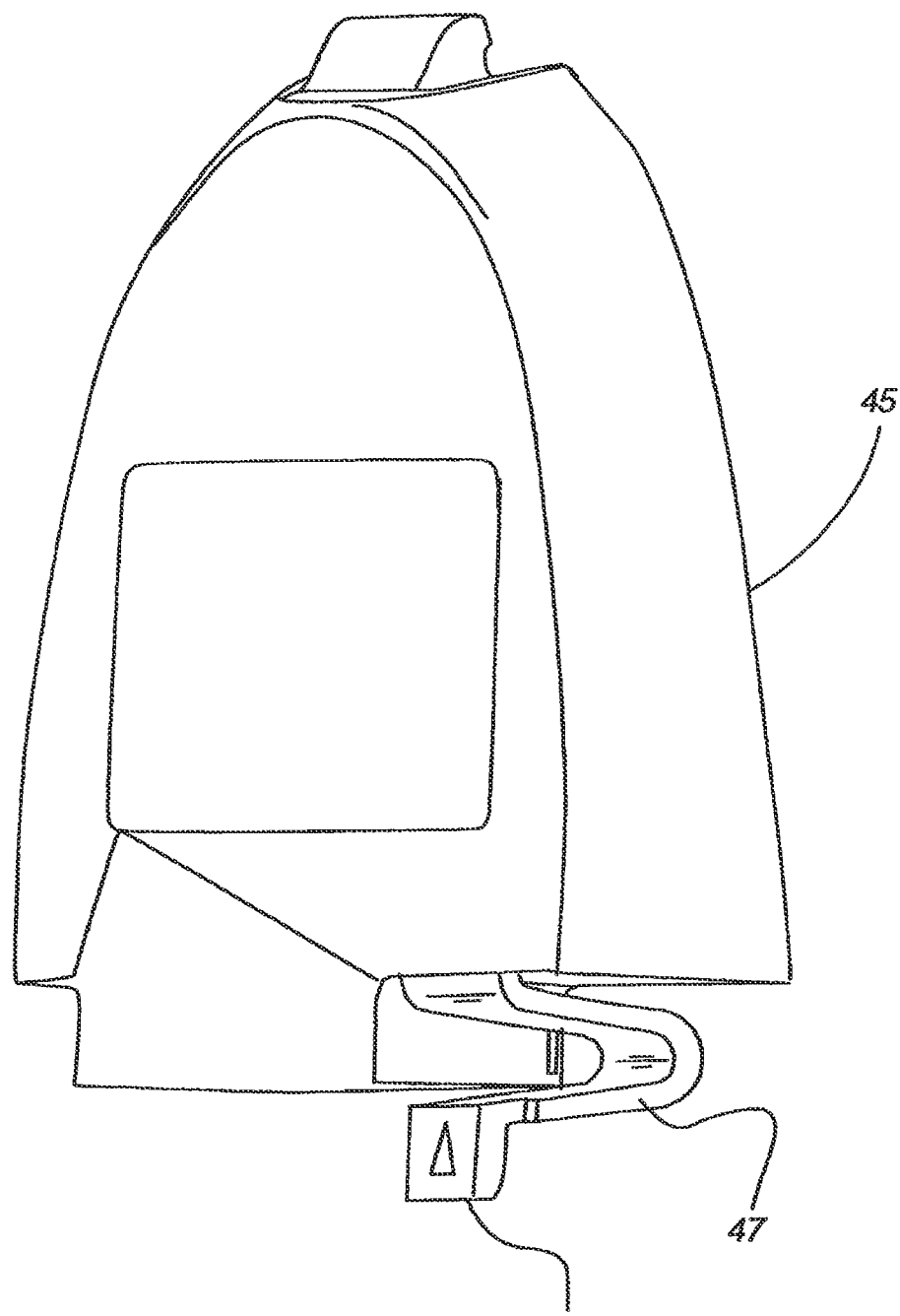
FIG. 25 is a bottom perspective view of a reservoir of the handheld oral irrigator.

For a discussion regarding disengaging the reservoir 45 from the rest of the handle portion, reference is made to FIGS. 8 and 25, wherein FIG. 25 is a bottom perspective view of the reservoir of the handheld oral irrigator. As best shown in FIGS. 8 and 25, the reservoir 45 includes a leaf spring latch 47 molded into a lower portion of the reservoir 45 to releasably secure the reservoir 45 to the handle portion 15. The leaf spring latch 47 is biased to engage the handle portion 15 when the reservoir 45 is joined with the handle portion 15. To disengage the leaf spring latch 47 from the handle portion 15, the user moves a latch portion 49 of the leaf spring latch 47 in the direction indicated by an arrow formed, printed, or placed on the leaf spring latch 47. In one embodiment, the reservoir 45 moves downwardly relative to the handle portion 15 when the leaf spring latch 47 is disengaged from the handle portion 15.

Referring again to FIGS. 1, 3 and 5-7 for a continued discussion of the overall external configuration of the handheld oral irrigator, in one embodiment, a control side of the gripping area 35 includes an on/off control 52, a pressure control 54, and a removable faceplate 56 that surrounds the locations of the two controls 52, 54. The on/off control 52 allows a user to turn on or shut off the irrigator 10. To turn the irrigator 10 on, the on/off control 52, which can be a slide, button, etc., is moved (e.g., slid or depressed) to complete an electrical circuit between the irrigator's internal power source and its motor. To turn the irrigator 10 off, the control 52 is moved again to break the electrical circuit.

The pressure control 54 allows a user to adjust the discharge pressure of a fluid stream discharging from the distal tip of the nozzle 20. In one embodiment, the nozzle release button 25 is located on the reservoir side opposite from the controls 50, 52, which helps limit accidental release of the nozzle 20 by accidental pressing or other engagement of the nozzle release button 25 when the user operates the controls 50, 52.

The removable faceplate 56 can be replaced with other faceplates having other colors or designs, thereby allowing the user to customize the appearance of the irrigator 10 as preferred. In one embodiment, the handheld oral irrigator 10 is sold or provided with multiple faceplates 56 of various designs and colors. The user selects their preferred faceplate and mounts it on the handle portion 15.

Figure 26:
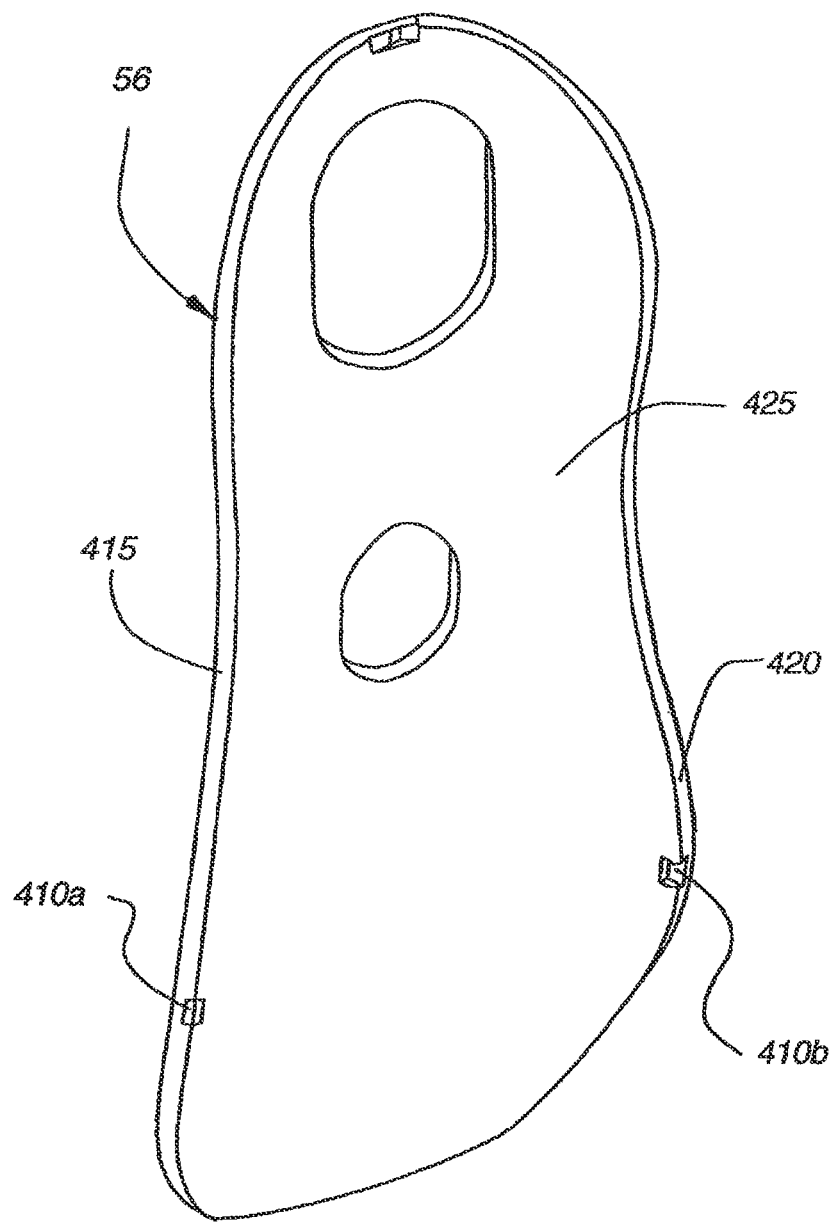
FIG. 26 is a rear perspective view of a removable faceplate of the handheld oral irrigator.

As shown in FIG. 26, which is a rear perspective view of the removable faceplate of the handheld oral irrigator, the removable face plate 56 has two or more L-shaped tabs 410a, 410b for receipt in corresponding slots or grooves defined in the handle portion 15 of the oral irrigator 10 to join the removable faceplate 56 to the handle portion 15. When joined together, the short legs of the tabs 410a, 410b are received in the slots or grooves defined in the handle portion 15 to maintain the joined relationship between the removable faceplate 56 and the handle portion 15.

To disconnect the removable faceplate 56 from the handle portion 15, the removable faceplate 56 is sufficiently flexible such that a user can deflect the edges 415, 420 of the removable faceplate 56 inward in order disengage the tabs 410a, 410b from the handle portion 15 to pull the faceplate 56 away from the handle portion 15. As a user moves the edges 415, 420 of the removable faceplate 56 inwardly, the short legs of the tabs 410a, 410b are removed from the slots or grooves in the handle portion 15, thereby allowing the user to remove the removable faceplate 56 from the handle portion 15.

To join the removable faceplate 56 to the handle portion 15, a user deflects the edges 415, 420 of the removable faceplate 56 inwardly and abuts a rear facing surface 425 of the removable faceplate 56 against the handle portion 15. When the removable faceplate 56 abuts the handle portion 15 in the proper location and orientation, the short legs of the tabs 410a, 410b generally align with the grooves or slots in the handle portion 15. In one embodiment, the handle portion 15 has a recessed surface surrounding the controls 50, 52 to aid a user in properly locating and orienting the removable faceplate 56 relative to the handle portion. 15. Once the removable faceplate 45 abuts the handle portion 56 in the proper location and orientation, the user stops squeezing the edges 415, 420 of the removable faceplate inwardly, thereby causing the short legs of the tabs 410a, 410b, which are biased to move outwardly by the internal forces generated by inward movement of the edges 415, 420 of the removable faceplate 56, to enter into the grooves or slots defined in the handle portion 15.

Referring again to FIGS. 1, 3 and 5-7 for a continued discussion of the overall external configuration of the handheld oral irrigator, the reservoir side of the gripping area 35 includes a soft over molded grip area 58, which in one embodiment, includes gripping bumps 60, a textured gripping surface, or other grip enhancing features.

As illustrated in FIGS. 1 and 3, in one embodiment, a charging plug 63 exits in the handle portion 15 near the base 30. The charging plug 63 is used to place an external power source in electrical communication with an internal power source (e.g., battery) located within the handle portion 15.

Figure 9:
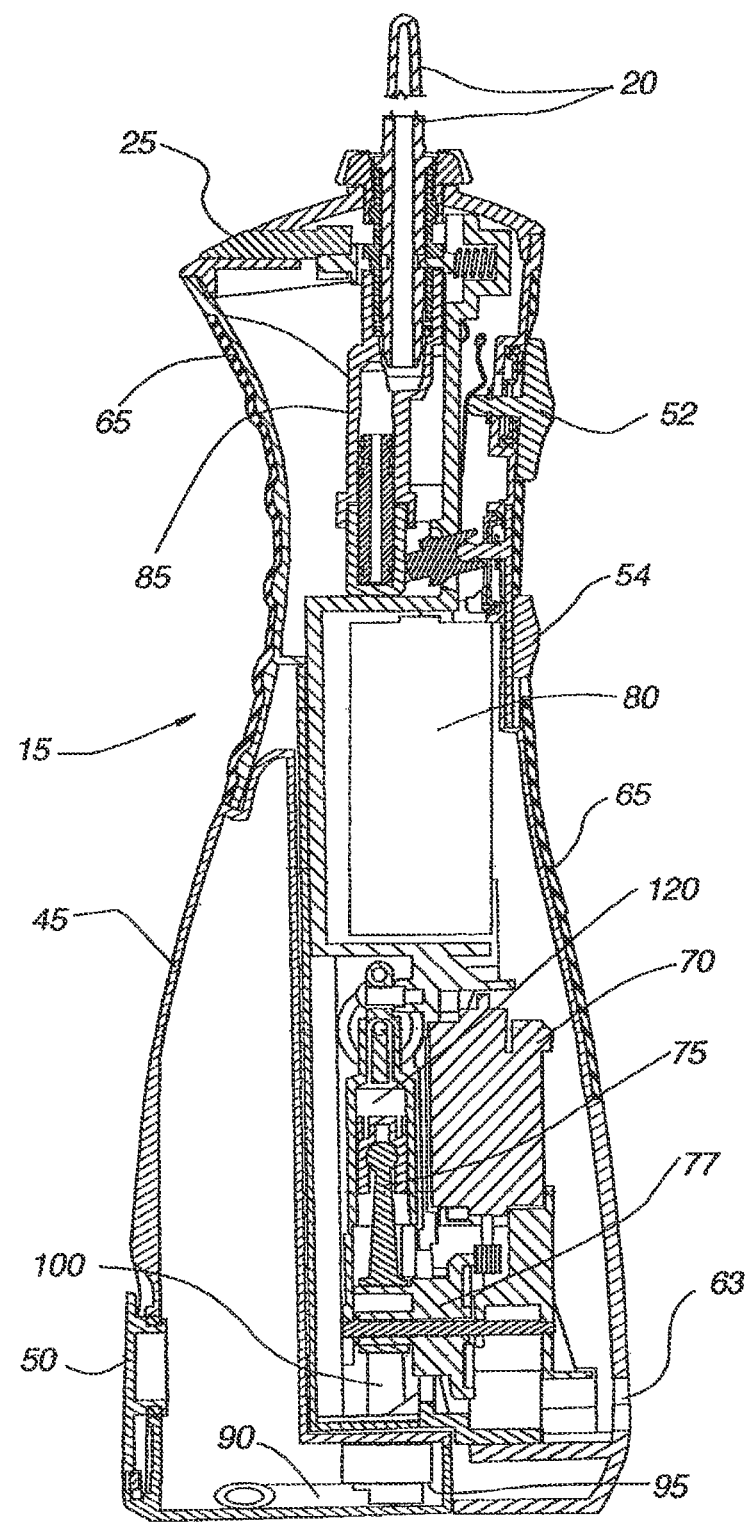
FIG. 9 is a section elevation of the handheld oral irrigator as taken along section line 9-9 in FIG. 4.
Figure 10:
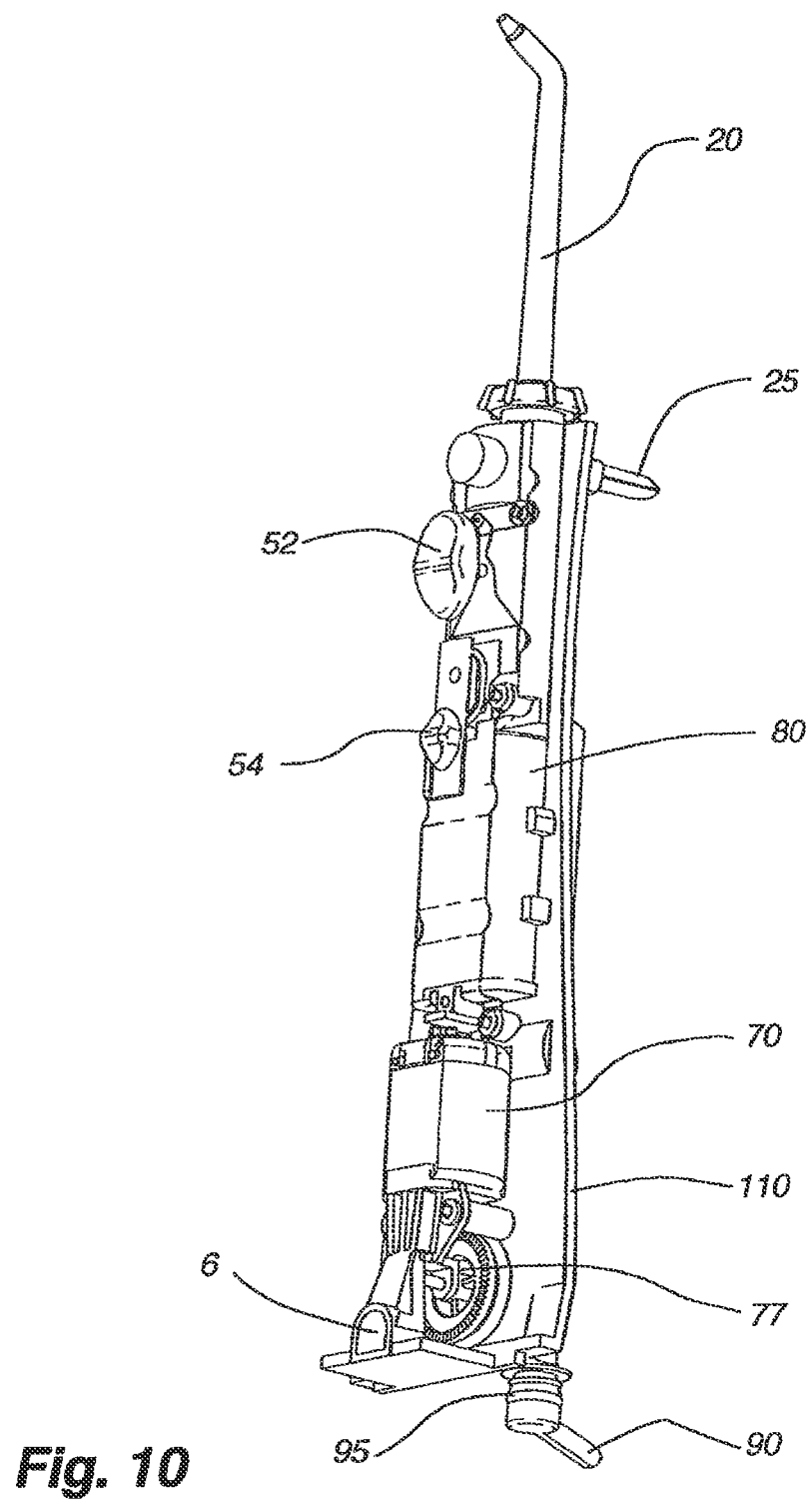
FIG. 10 is an isometric view of a motor side of the handheld oral irrigator with the outer housing of the handle portion removed to show the internal elements of the irrigator.
Figure 11:
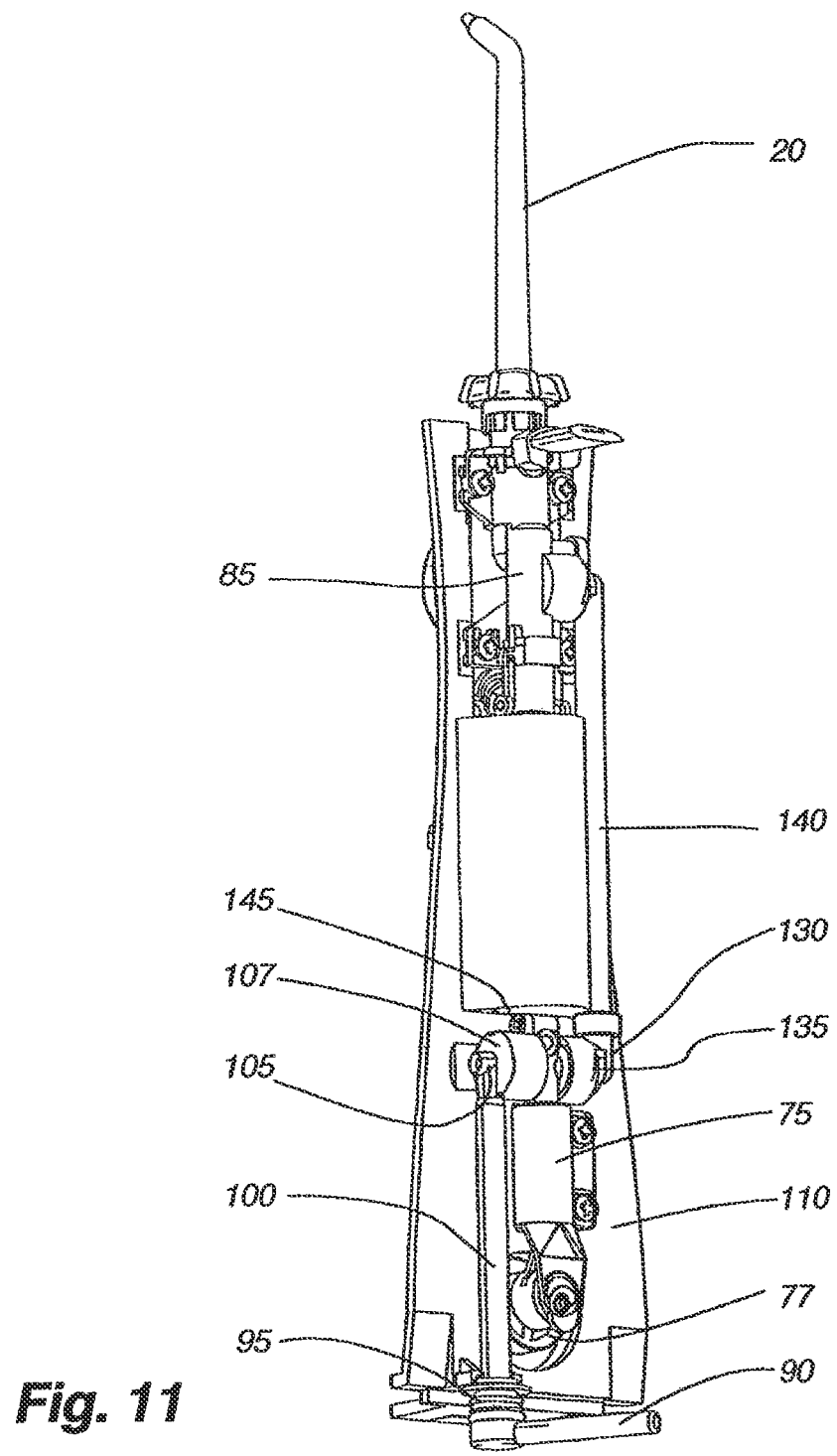
FIG. 11 is the same type of view as illustrated in FIG. 10, except of a pump side of the handheld oral irrigator.
Figure 23:
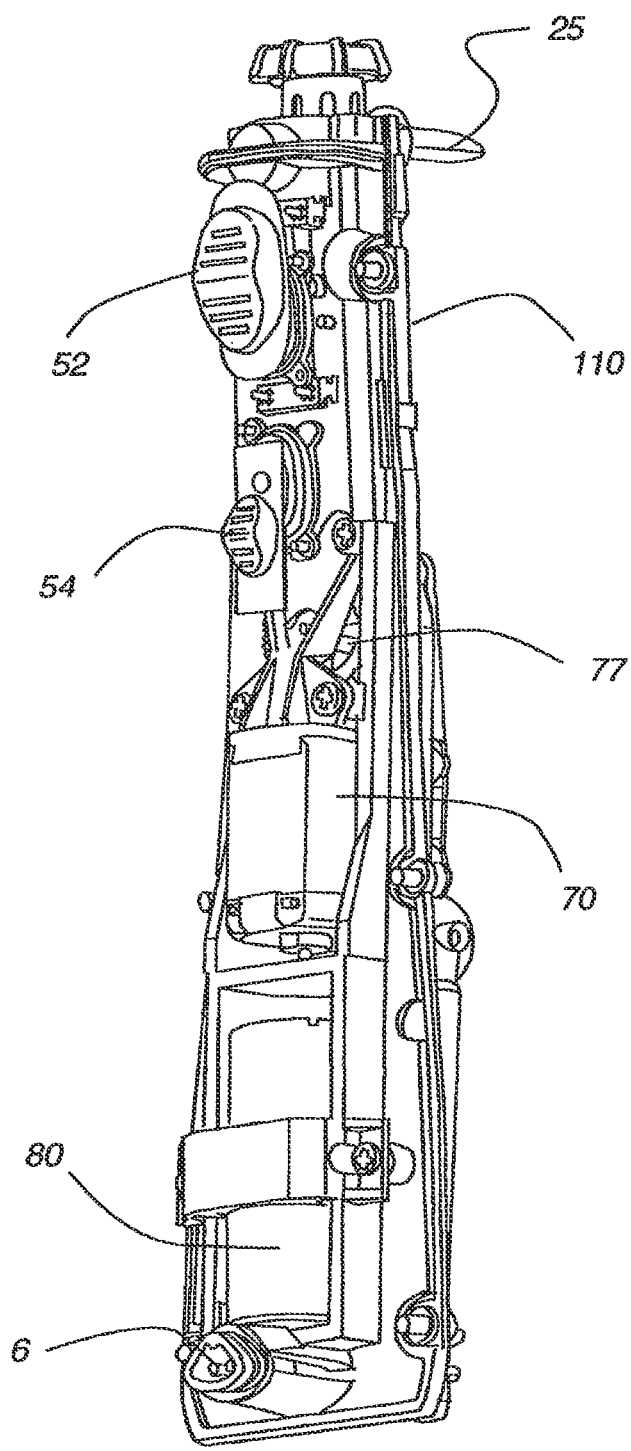
FIG. 23 is a similar view as illustrated in FIG. 10, except various components are shown in an alternate configuration.
Figure 24:
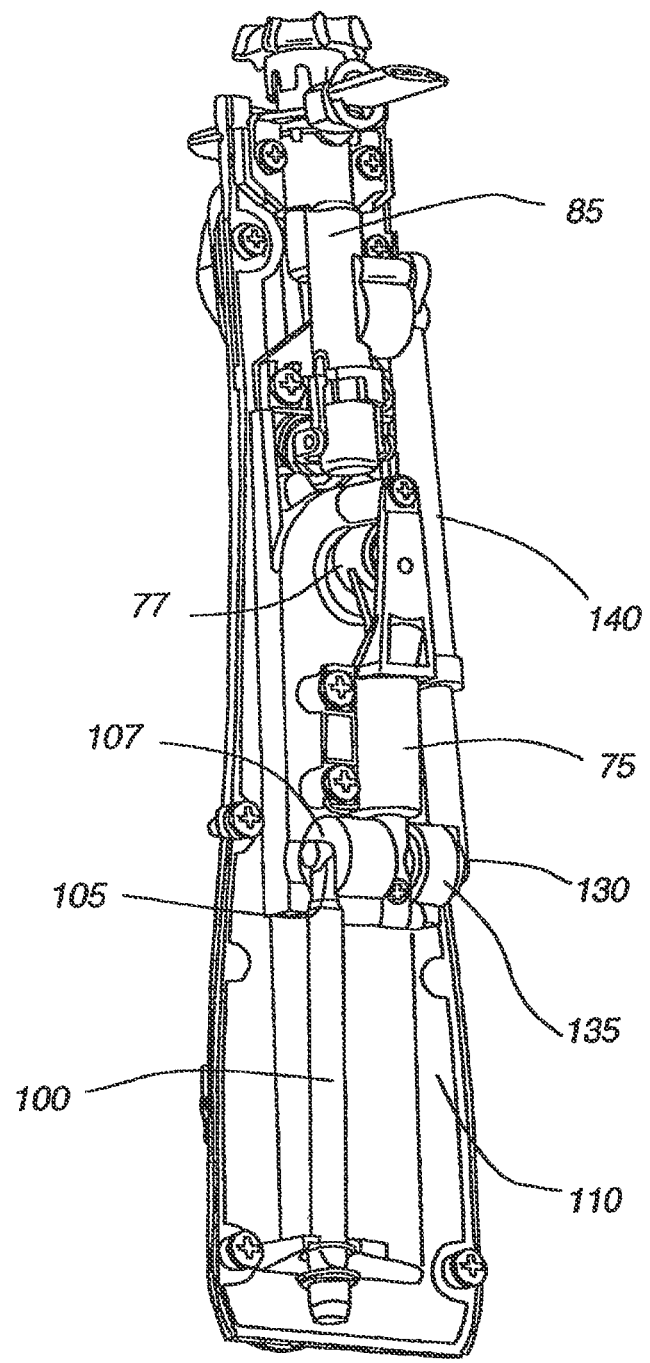
FIG. 24 is a similar view as illustrated in FIG. 11, except various components are shown in an alternate configuration.

For a discussion of the overall internal configuration of one embodiment of the handheld oral irrigator 10, reference is made to FIGS. 9-11, 23 and 24. FIG. 9 is a section elevation of the handheld oral irrigator 10 as taken along section line 9-9 in FIG. 4. FIG. 10 is an isometric view of a motor side of the handheld oral irrigator 10 with the outer housing 65 of the handle portion 15 removed to show the internal elements of the irrigator 10. FIG. 11 is the same type of view as illustrated in FIG. 10, except of a pump side of the handheld oral irrigator 10. FIG. 23 is a similar view as illustrated in FIG. 10, except various components are shown in an alternate configuration. FIG. 24 is a similar view as illustrated in FIG. 11, except various components are shown in an alternate configuration.

As shown in FIG. 9, the irrigator 10 includes an outer housing 65 that forms the exterior surface of the handle portion 15. The housing 65 encloses a motor 70, a pump 75, a transmission 77, a rechargeable NiCad battery 80, and a pressure control valve assembly 85. In one embodiment as illustrated in FIGS. 10 and 11, the motor 70 and pump 75 are located in a side-by-side arrangement near the base 30, the transmission 77 is located below the motor 70 and pump 75, the battery 80 is located above the motor 70 and pump 75, and the valve assembly 85 is located above the battery 80. In another embodiment as illustrated in FIGS. 23 and 24, the battery 80 is located near the base 30, the motor 70 and pump 75 are located above the battery 80, the transmission 77 is located above the motor 70 and pump 75, and the valve assembly 85 is located above the transmission 77. The transmission 77 couples the motor 70 to the pump 75 to convert the rotational output of the motor 70 into the longitudinally reciprocating movement of the pump's piston 120.

As illustrated in FIG. 9, the removable reservoir 45 forms a significant part of a lower side of the handle portion 15. The fill port 50 opens into the reservoir 45, and the reservoir 45 extends under a portion of the housing 65 enclosing the motor 70 and pump 75. A transfer tube 90 extends from a bottom level of the reservoir 45 to a seal coupling 95. In one embodiment, the transfer tube 90 is part of the reservoir. In another embodiment, the transfer tube 90 is separate from the reservoir 45. When the reservoir 45 is coupled to the rest of the handle portion 15, the seal coupling 95 sealing mates with a bottom end of a suction tube 100, which leads to a suction port 105 of the pump 75, as best understood from FIGS. 11 and 24. Thus, the reservoir 45 is placed in fluid communication with the suction side of the pump 75.

As indicated in FIGS. 10 and 11, and FIGS. 23 and 24, the motor 70, pump 75, transmission 77 and valve assembly 85 are coupled to a chassis plate 110 longitudinally extending through the housing 65 of the handle portion 15. In one embodiment, the controls 52, 54, motor 70 and the battery 80 are located on one side of the plate 110, and the pump 70 and valve assembly 85 are located on the other side of the plate 110.

As can be understood from FIGS. 9 and 11, the suction tube 100 is detachably sealably coupled to the seal coupling 95 by coupling the reservoir 45 to the rest of the housing 65 of the handle portion 15 such that the free end of the suction tube 100 is received in the seal coupling 95. As shown in FIG. 11, fluid traveling form the reservoir 45 to the distal end of the nozzle 20 is drawn through the transfer tube 90, into the suction tube 100 at the seal coupling 95 and to the suction port 105 of the pump 75.

Figure 12:
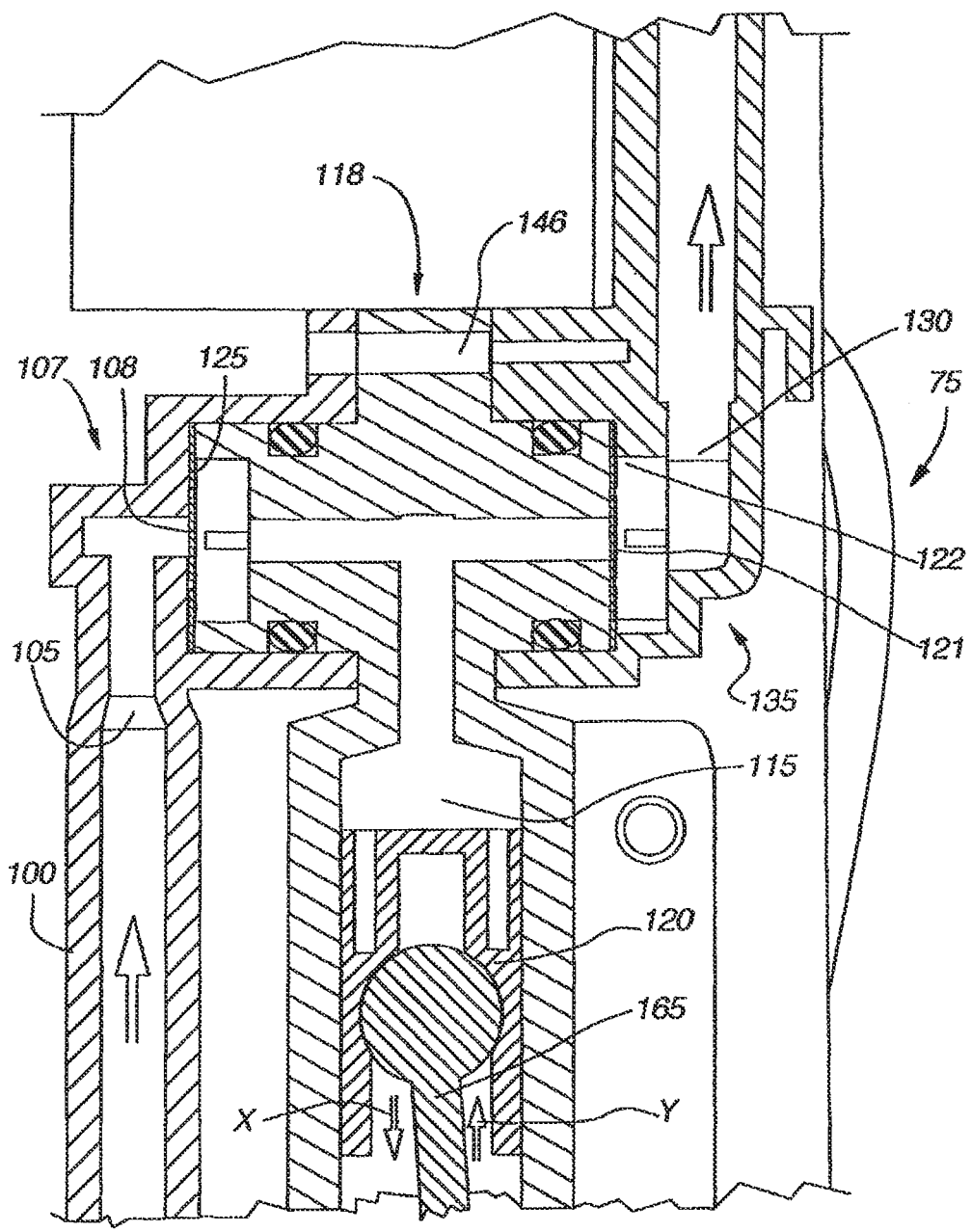
FIG. 12 is a longitudinal section through the pump.

As can be understood from FIG. 12, which is a longitudinal section through the pump 75, when a piston 120 moves rearwardly in a cylinder 115 of a cylinder casing 118 (rearward movement indicated by arrow X in FIG. 12), a discharge wafer 121 of a discharge wafer valve arrangement is forced against a discharge valve seat 122 and the fluid is drawn through the suction port 105 of a suction casing 107 of the pump 75, past a suction wafer 108 forming a suction wafer valve arrangement, and into the cylinder 115. When the piston 120 moves forwardly (as indicated by arrow Y in FIG. 12), the suction wafer 108 is forced against the suction valve seat 125 and the fluid is forced past the discharge wafer 121, into a discharge port 130 of a discharge casing 135 of the pump 75, and into a discharge tube 140 leading to the valve assembly 85, as illustrated in FIGS. 11 and 24.

In one embodiment, as depicted in FIGS. 11 and 12, the pump 75 is formed from three casings (e.g., the suction casing 107, cylinder casing 118 and discharge casing 135). In one embodiment, the three casings 107, 118, 135 are held together via a joining mechanism. For example, in one embodiment, a screw 145 (illustrated in FIG. 11) is received in screw receiving holes 146 (shown in FIG. 12) in the three casings 107, 118, 135.

Figure 13:
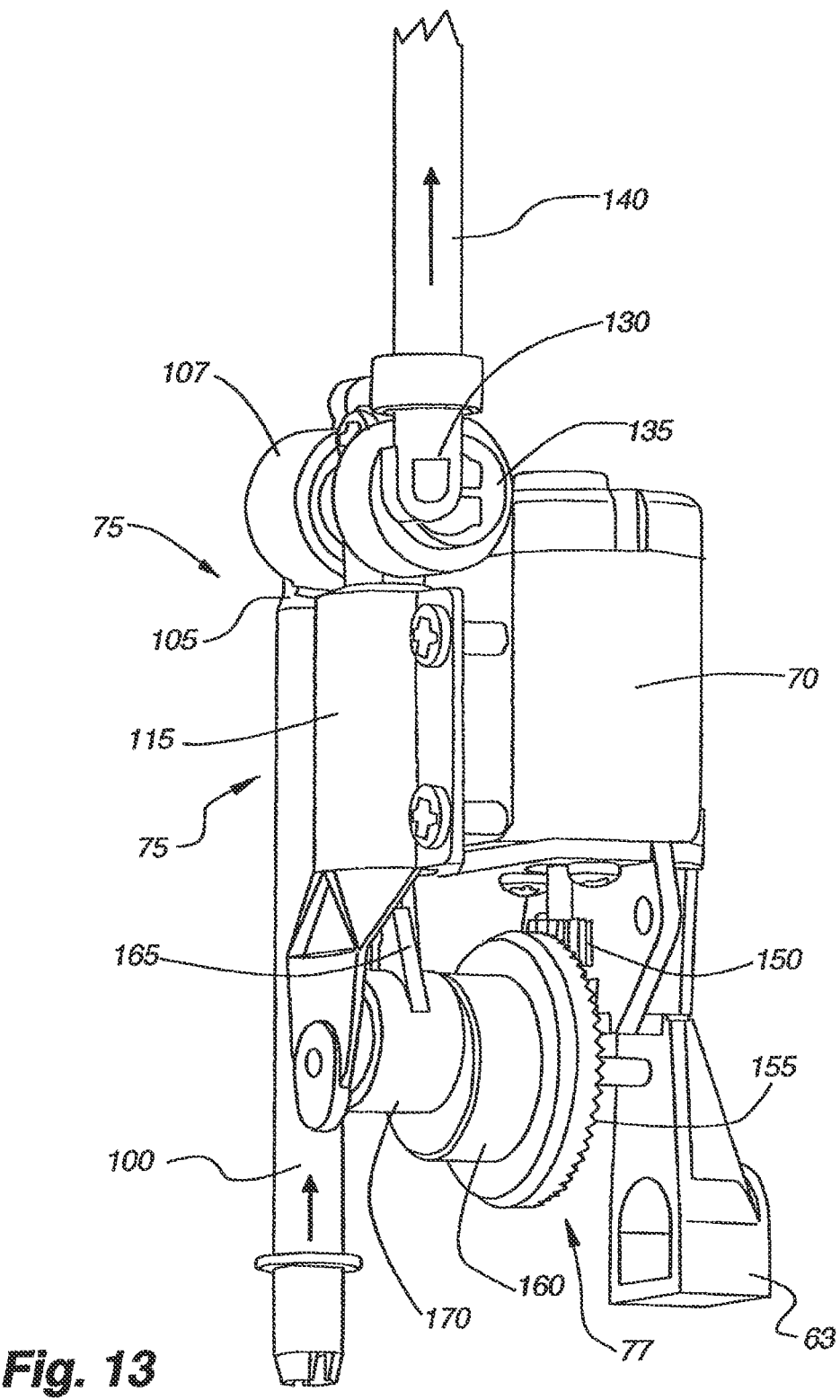
FIG. 13 is an isometric of view of the motor/pump/transmission arrangement with the rest of the irrigator 10 hidden for clarity purposes.

For a discussion of the motor/pump/transmission arrangement, reference is made to FIG. 13, which is an isometric view of the motor/pump/transmission arrangement with the rest of the irrigator 10 hidden for clarity purposes. As shown in FIG. 12, a pinion gear 150 extends from the motor 70 to drive a gear 155 carrying a cam 160. A piston rod 165 (see FIGS. 12 and 13) extends between the piston 120 and a cam follower end 170 of the piston rod 165. The cam follower end 170 receives the cam 160, and as the cam 160 is caused to rotate, the cam follower 170 and cam 160 act to convert the rotational movement of the motor 70 into longitudinal reciprocal displacement of the piston 120 within the cylinder 115.

Figure 14:
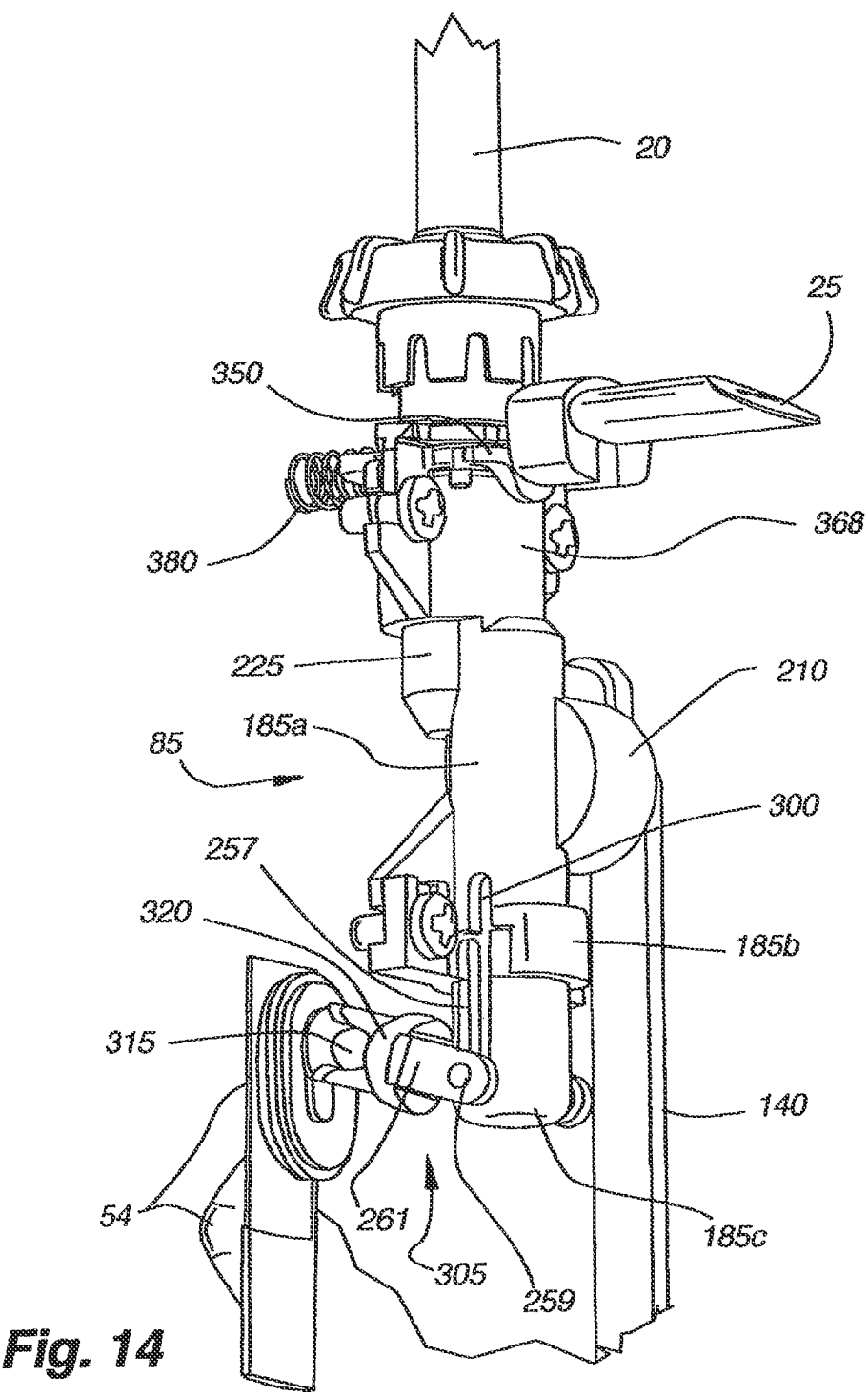
FIG. 14 is an isometric view of the pressure control valve assembly 85 with the majority of the rest of the handheld oral irrigator 10 hidden for clarity purposes.
Figure 15:
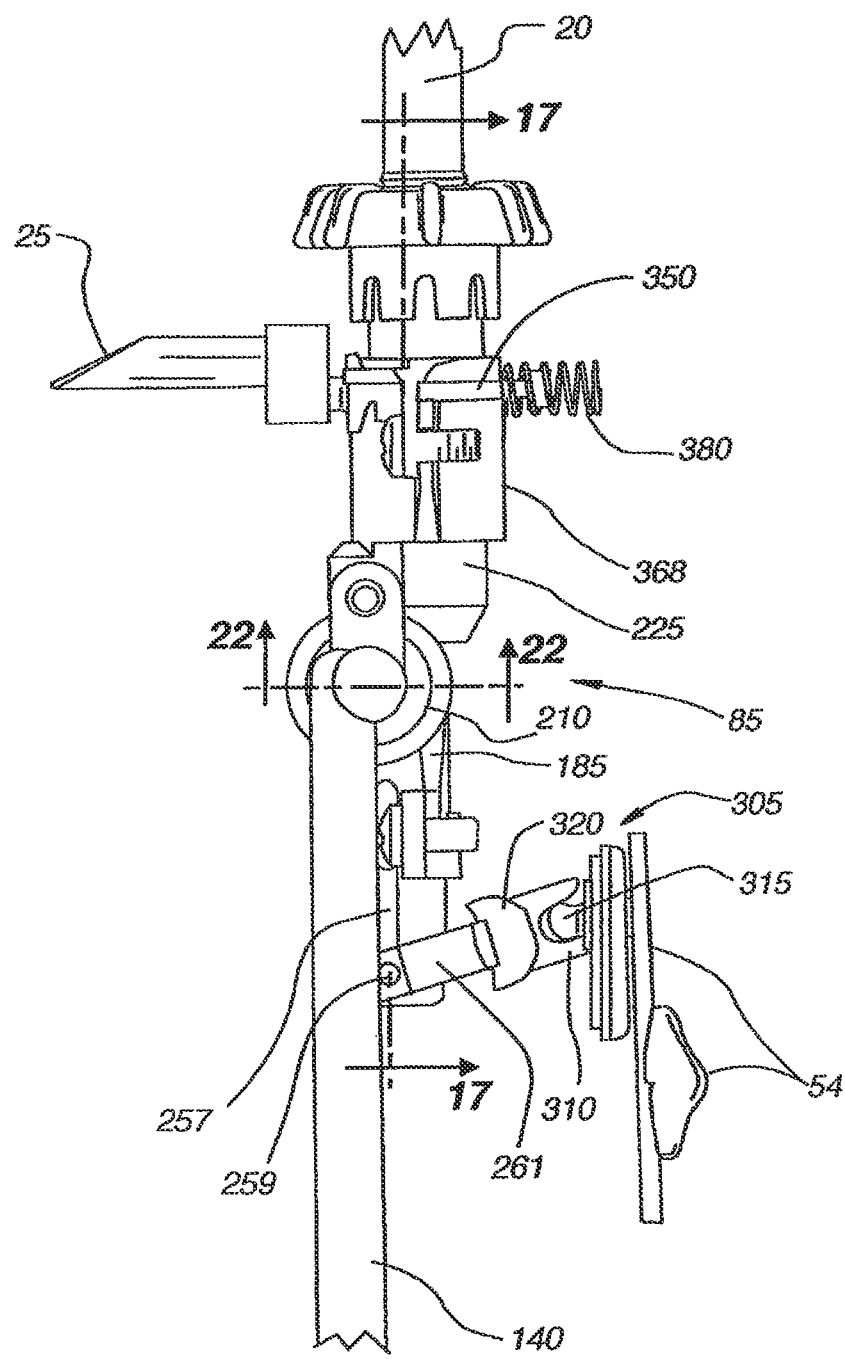
FIG. 15 is a side elevation of the same elements depicted in FIG. 14, as viewed from the same direction as FIG. 6.
Figure 16:
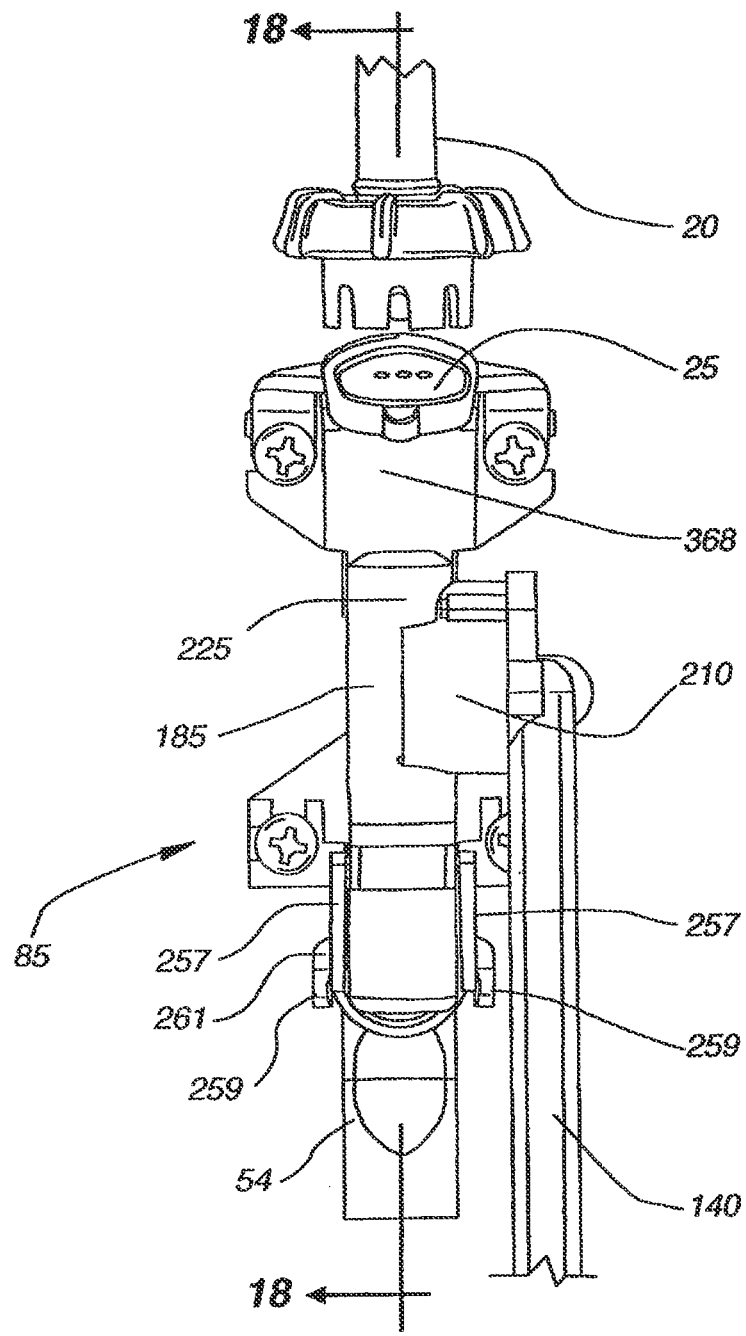
FIG. 16 is a side elevation of the same elements depicted in FIG. 14, as viewed from the same direction as FIG. 4.
Figure 17A:
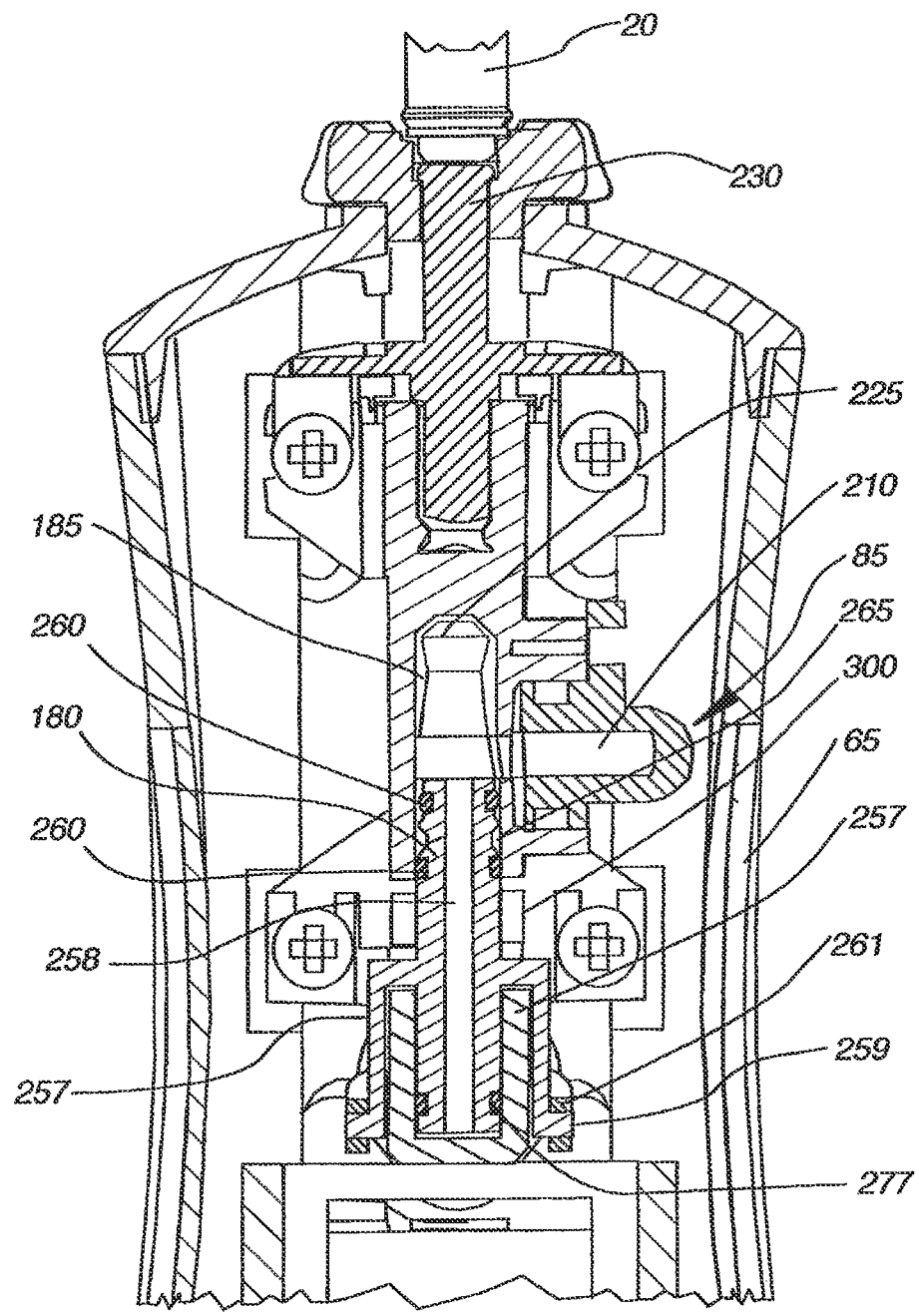
FIG. 17A is a longitudinal cross section of the pressure control valve assembly as taken along section line 17-17 in FIG. 15 and wherein a spool is in a rearward location (i.e., a high discharge pressure position) within the valve cylinder.
Figure 17B:
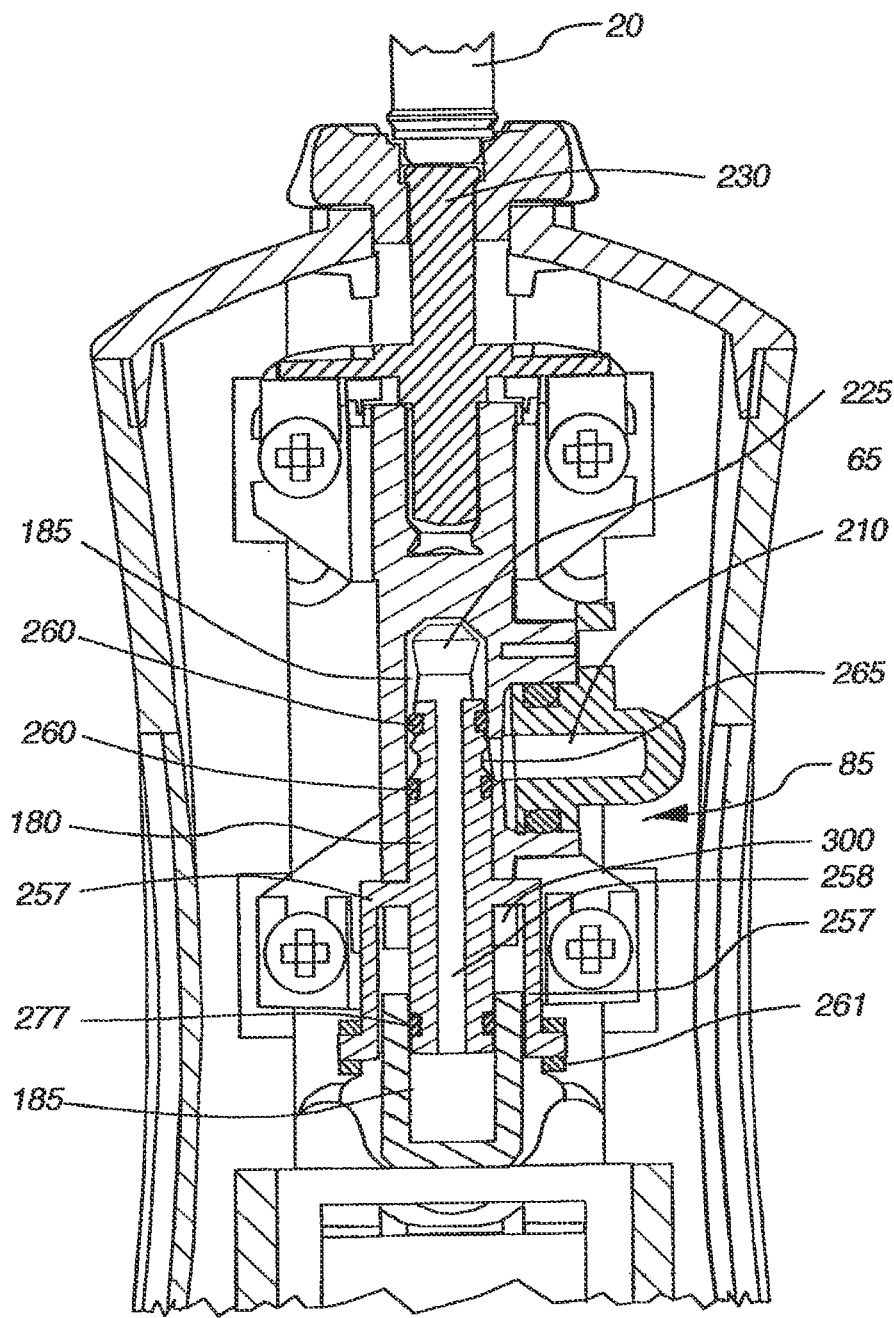
FIG. 17B is the same view depicted in FIG. 17A, except the spool is in a forward location (i.e., a low discharge pressure position) within the valve cylinder.
Figure 18A:
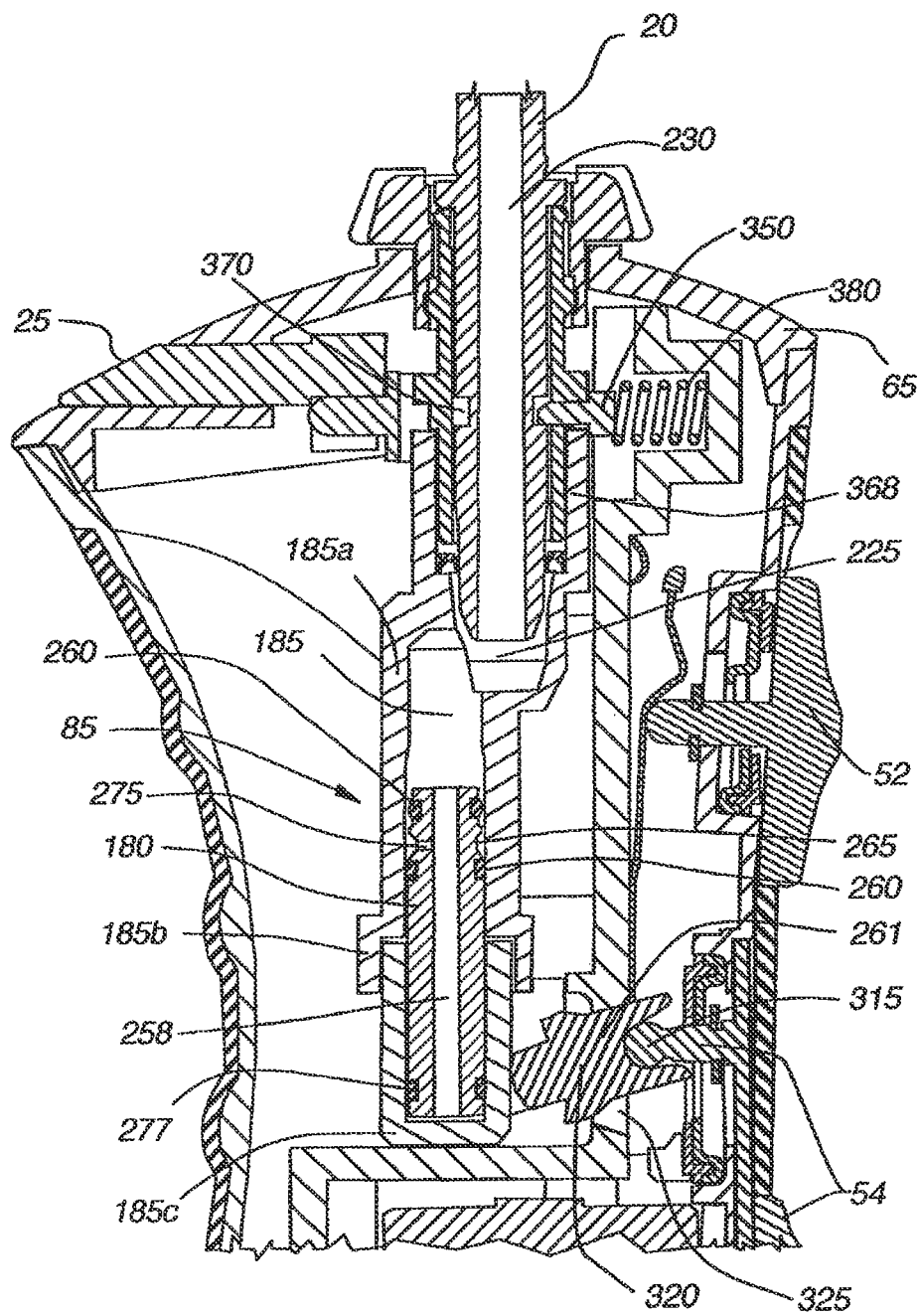
FIG. 18A is a longitudinal cross section of the pressure control valve assembly as taken along section line 18-18 in FIG. 16 and wherein the spool is in a rearward location (i.e., a high discharge pressure position) within the valve cylinder.
Figure 18B:
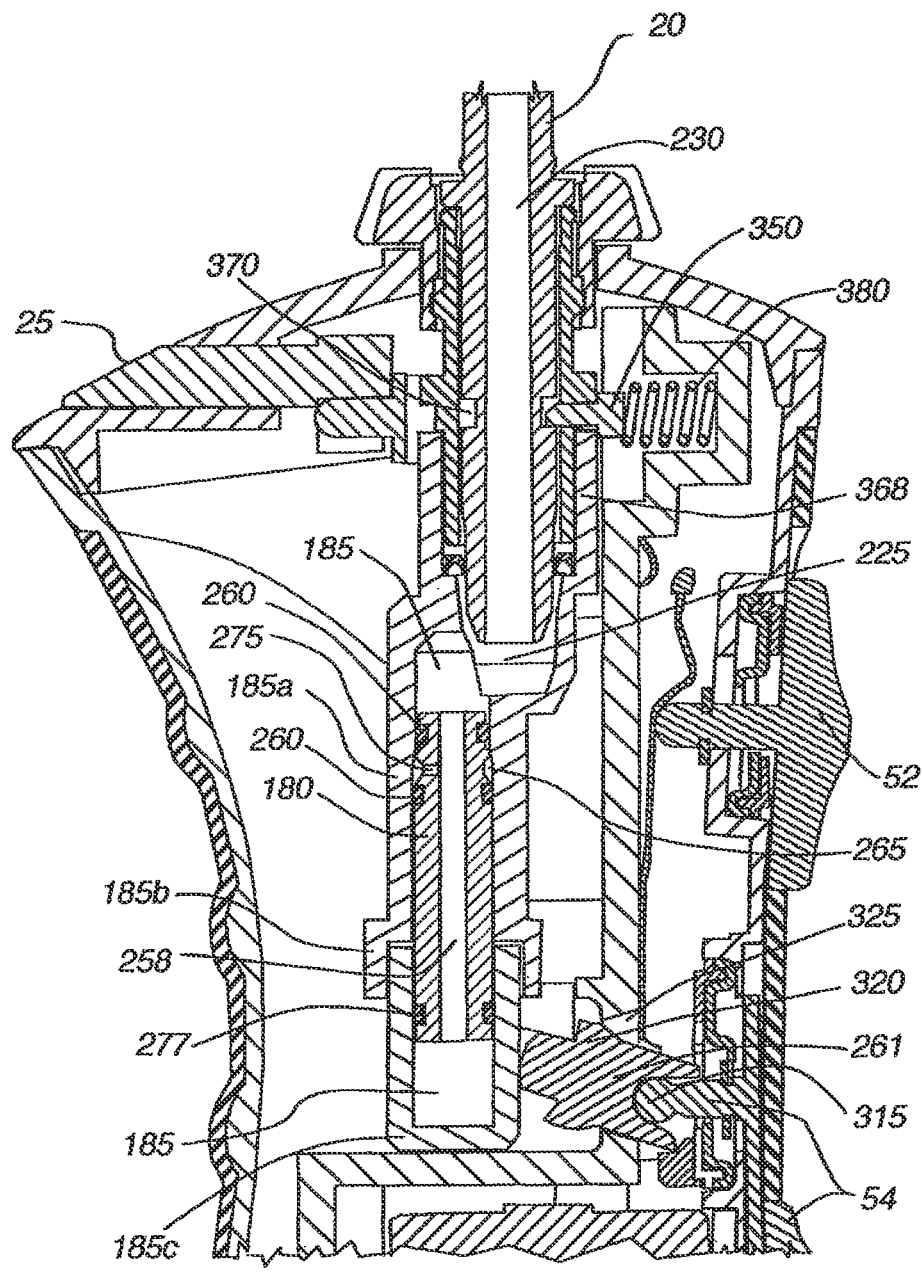
FIG. 18B is the same view depicted in FIG. 18A, except the spool is in a forward location (i.e., a low discharge pressure position) within the valve cylinder.
Figure 19:
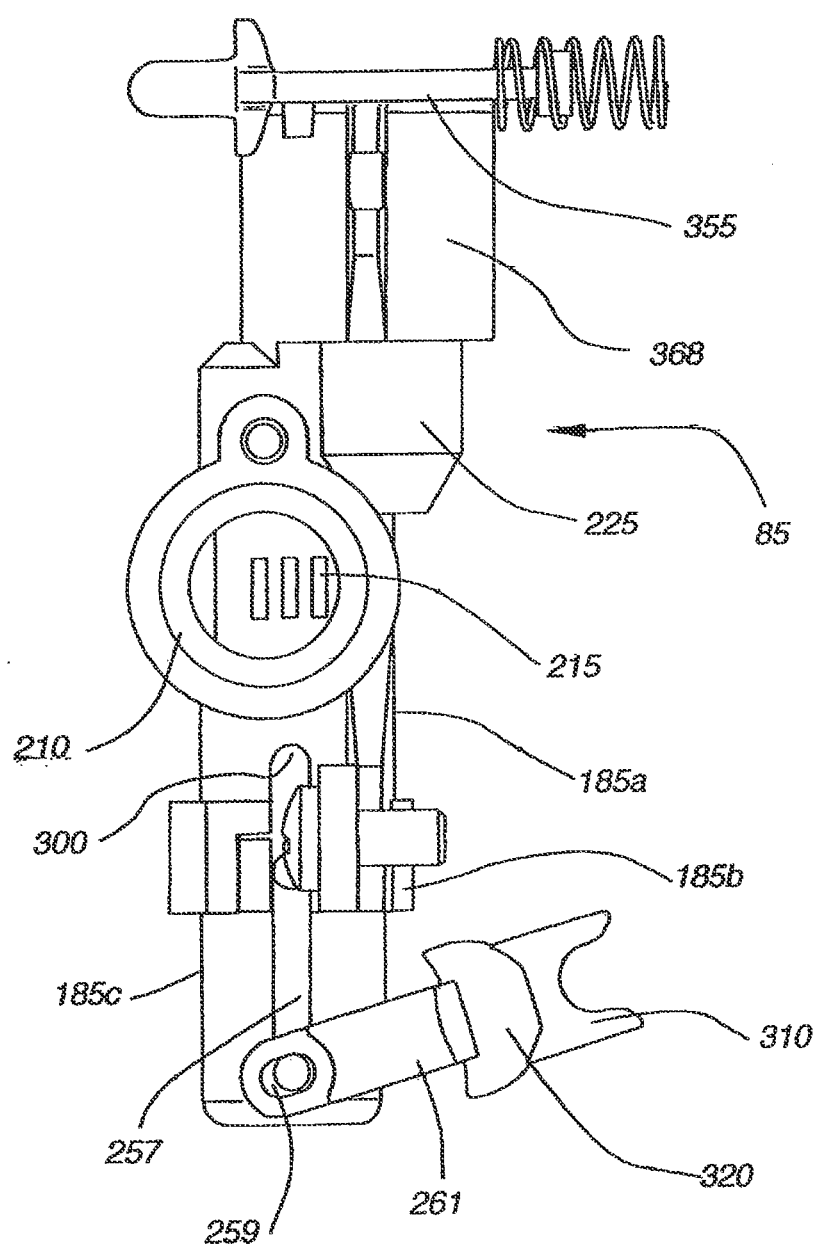
FIG. 19 is a side view of the pressure control valve assembly as shown in FIG. 15, except the discharge tube, nozzle and control button are hidden for clarity purposes.
Figure 20:
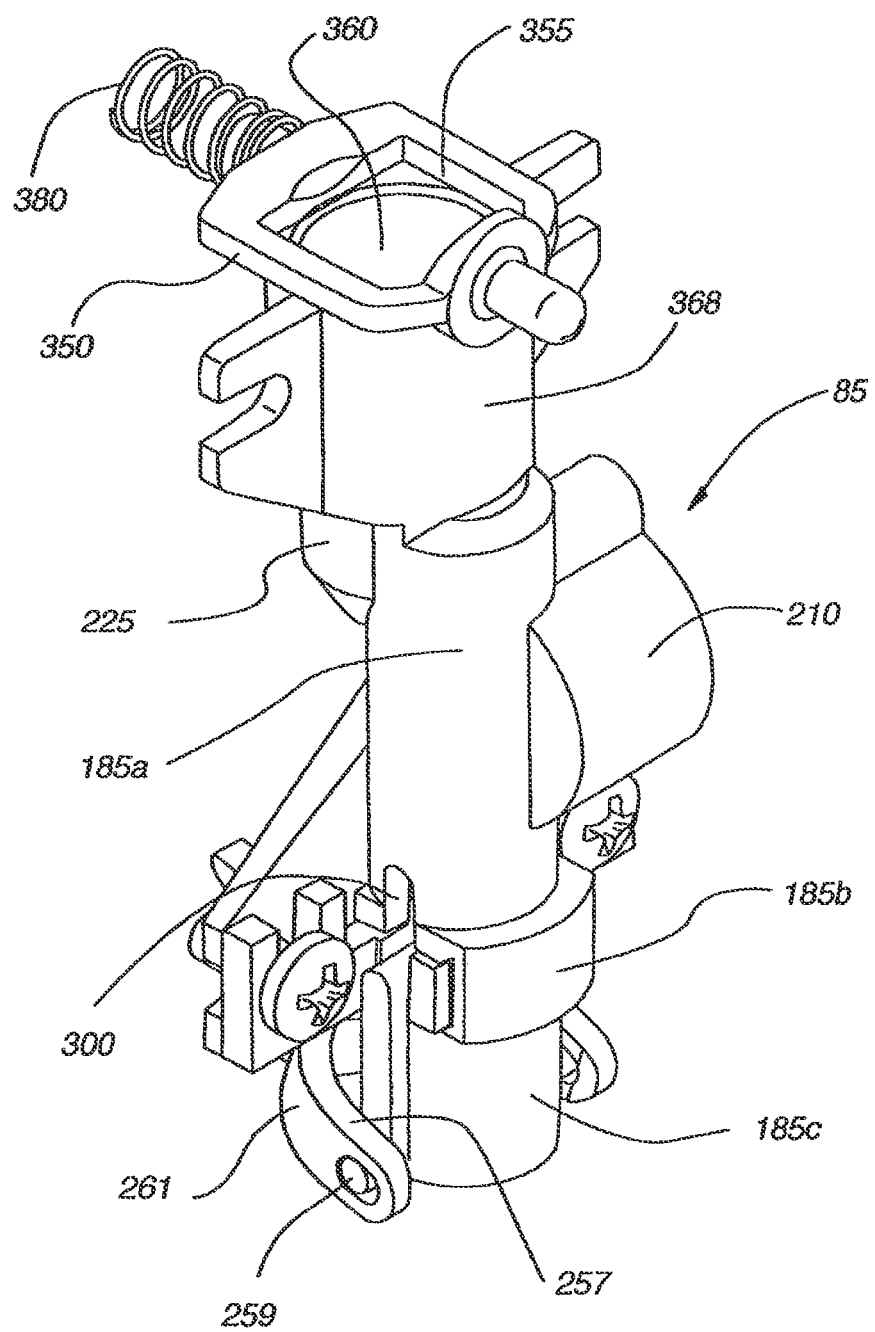
FIG. 20 is an isometric view of the valve assembly wherein the discharge tube, nozzle and control button are hidden for clarity purposes.
Figure 21:
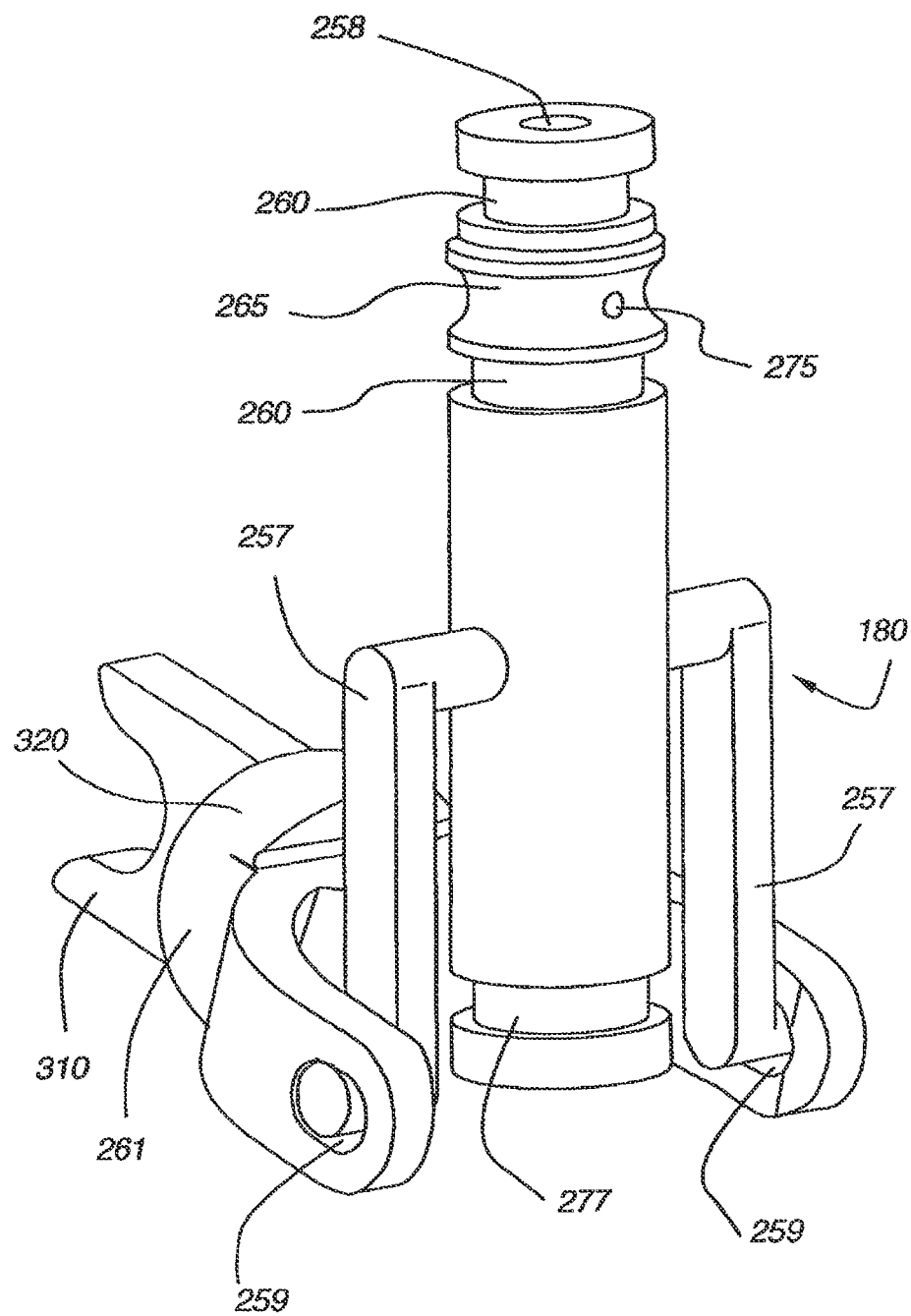
FIG. 21 is an isometric view of the spool and yoke.
Figure 22:
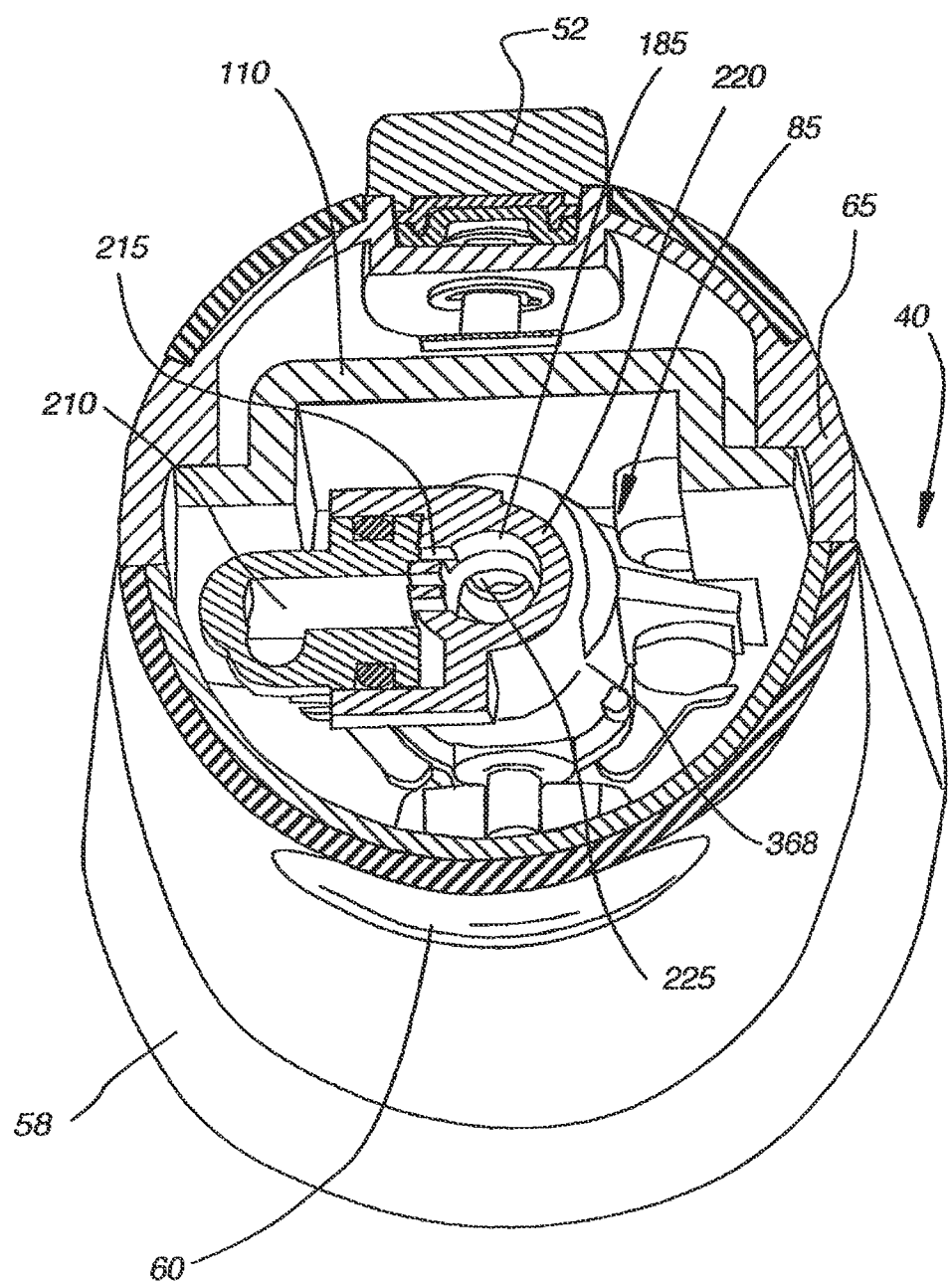
FIG. 22 is an isometric latitudinal cross section taken along section line 22-22 in FIG. 15.

For a discussion of the pressure control valve assembly 85, reference is made to FIGS. 14-22. FIG. 14 is an isometric view of the pressure control valve assembly 85 with the majority of the rest of the handheld oral irrigator 10 hidden for clarity purposes. FIG. 15 is a side elevation of the same elements depicted in FIG. 14, as viewed from the same direction as FIG. 6. FIG. 16 is a side elevation of the same elements depicted in FIG. 14, as viewed from the same direction as FIG. 4. FIG. 17A is a longitudinal cross section of the pressure control valve assembly 85 as taken along section line 17-17 in FIG. 15 and wherein a spool 180 is in a rearward location (i.e., a high discharge pressure position) within the valve cylinder 185. FIG. 17B is the same view depicted in FIG. 17A, except the spool 180 is in a forward location (i.e., a low discharge pressure position) within the valve cylinder 185. FIG. 18A is a longitudinal cross section of the pressure control valve assembly 85 as taken along section line 18-18 in FIG. 16 and wherein the spool 180 is in a rearward location (i.e., a high discharge pressure position) within the valve cylinder 185. FIG. 18B is the same view depicted in FIG. 18A, except the spool 180 is in a forward location (i.e., a low discharge pressure position) within the valve cylinder 185. FIG. 19 is a side view of the pressure control valve assembly 85 as shown in FIG. 15, except the discharge tube 140, nozzle 20 and control button 54 are hidden for clarity purposes. FIG. 20 is an isometric view of the pressure control valve assembly 85 wherein the discharge tube 140, nozzle 20 and control button 54 are hidden for clarity purposes. FIG. 21 is an isometric view of the spool 180 and yoke 190. FIG. 22 is an isometric latitudinal cross section taken along section line 22-22 in FIG. 15.

As can be understood from FIGS. 14-18B and 22, fluid pumped through the discharge tube 140 from the pump 75 enters an inlet 210 of the pressure control valve assembly 85. As depicted in FIG. 19 and FIG. 22, in one embodiment, to enter the valve cylinder 185, the fluid passes through slot openings 215 in the cylinder wall 220.

As can be understood from FIGS. 17A-18B, a spool 180 is located in the cylinder 185 and longitudinally displaceable within the cylinder 185. As illustrated in FIG. 21, the spool 180 is cylindrically shaped with a pair of arms 257 extending outwardly and rearwardly from a middle portion of the spool 180. A lumen 258 extends longitudinally through the length of the spool 180. The free ends of the arms 257 are received in pivot holes 259 in a yoke 261. The distal end of the spool 180 includes a pair of o-ring receiving grooves 260, a fluid groove 265 positioned between the o-ring grooves 260, and an orifice 275 extending between the fluid groove 265 and the lumen 270. The proximal end of the spool 180 includes an o-ring receiving groove 277.

As indicated in FIGS. 17A and 18A, when the spool 180 is located rearwardly in the cylinder 185, the fluid passes through the slot openings 215 (see FIGS. 19 and 20) and directly from the front of the cylinder 185, through the valve assembly outlet 225, through the lumen 230 of the nozzle 20, and out the distal tip of the nozzle 20 as a high discharge pressure fluid stream. As indicated in FIGS. 17B, 18B and 21, when the spool 180 is located forwardly in the cylinder 185, the fluid passes through the slot openings 215 (see FIGS. 19 and 20) and between the fluid groove 265 and the inner circumferential surface of the cylinder 185, through the orifice 275, into the lumen 258 of the spool 180, through the valve assembly outlet 225, through the lumen 230 of the nozzle 20, and out the distal tip of the nozzle 20 as a low discharge pressure fluid stream.

As can be understood from FIGS. 17A-20, when the spool 180 is in the forward position within the cylinder 185 (i.e., the low discharge pressure position), the fluid flow passing through the pressure control valve assembly 85 must overcome a substantially increased frictional resistance as compared to when the spool 180 is in the rearward position within the cylinder 185 (i.e., the high discharge pressure position). Accordingly, when the spool 180 is in the low discharge pressure position, the pressure control valve assembly 85 creates a substantially high-pressure drop in the fluid flow passing through the assembly 85 as compared to when the spool 180 is in the high discharge pressure position. Thus, without having to adjust the operating speed of the pump 75, a user may adjust the discharge pressure of a fluid stream emanating from the nozzle 20 of the oral irrigator 10 by adjusting the position of the spool 180 within the cylinder 185. Accordingly, the discharge pressure may be substantially modified by a user without causing a substantial change in the preferred pulse rate of the fluid stream.

As can be understood from FIGS. 17A-20, moving the spool 180 from the high discharge pressure position (see FIGS. 17A and 18A) to the low discharge pressure position (see FIGS. 17B and 18B) modifies, in several ways, the fluid flow path through the discharge pressure control assembly 85 and, as a result, the fluid flow path between the pump 75 and the nozzle 20. First, moving the spool 180 from the high to the low discharge pressure position increases the length of the fluid flow path because the flow is diverted about the fluid groove 265, through the orifice 275 and through the lumen 258 before the flow can pass through the cylinder outlet 225 to the nozzle 20. Second, moving the spool 180 from the high to the low discharge pressure position substantially decreases the diameters or flow areas of the fluid flow path because the diameters or flow areas of the fluid groove 265, orifice 275, and lumen 258 are substantially smaller than the internal diameter or flow area of the cylinder 185. Third moving the spool 180 from the high to the low discharge pressure position increases the number of direction deviations the fluid flow must undergo because the fluid must travel a tortuous route around the groove 265 and through the orifice 275 and lumen 258 before the flow can pass through the cylinder outlet 225 to the nozzle 20.

Each of these modifications to the fluid flow path brought about by moving the spool 180 from the high to low discharge pressure position increases the magnitude of the fluid flow friction between the pump 75 and the nozzle 20. Accordingly, although the pump 75 continues to operate at generally the same speed and provides a fluid stream at generally the same pulse rate, because the spool 180 moves from the high to the low discharge pressure position within the cylinder 185, the discharge pressure of the fluid stream at the distal end of the nozzle 20 decreases from a high to low discharge pressure.

Research has indicated that some fluid stream pulse rates are more effective than other pulse rates. For example, in one embodiment, the pump 75 of the oral irrigator 10 cycles at a rate such that it discharges a fluid stream out the nozzle 20 that has a pulse rate of 1000-1600 pulses per minute and, in one embodiment, 1100-1400 pulses per minute and, in one embodiment, 1200 pulses per minute. As discussed in U.S. Pat. No. 3,227,158 issued to Mattingly, which is incorporated by reference herein in its entirety, a pulse rate of 1000-1600 pulses per minute has been found to be the most effective pulse rates for the purposes of oral hygiene and health. Other highly effective pulse rates for the purposes of oral hygiene and health also include 1100-1400 pulse per minute and 1200 pulses per minute.

The pressure control feature is advantageous because it allows a user to adjust the fluid stream discharge pressure to suit the user's comfort preferences while maintaining the pulse rate generally at a preferred pulse rate. For example, regardless of whether the pressure control valve assembly 85 is set to cause a low or high discharge pressure fluid stream to emanate from the nozzle 20, the fluid stream will have a preferred number of pulses per minute (e.g., 1000-1600 pulses per minute, 1100-1400 pulses per minute, 1200 pulses per minute, etc.).

For a discussion of the cylinder's configuration, reference is again made to FIGS. 14 and 17A-20. As best understood from FIGS. 14, 19 and 20, the cylinder 185 of the pressure control valve assembly 185 includes a proximal portion 185a received within a collar portion 185b of a distal portion 185c. A slot 300 extends longitudinally along the sides of the cylinder 185, and the arms 257 of the spool 180 extend through the slots 300 to couple with the arms of the yoke 261. As indicated in FIGS. 17A-18B, the cylinder 185 is hollow to receive the spool 180, and the proximal end of the cylinder proximal portion 185c is walled-off such that when a fluid flows into the lumen 258 of the spool 180, the fluid impacts the proximal end of the cylinder proximal portion 185c to establish a back pressure condition within the pressure control valve assembly 85. As can be understood from FIGS. 17A and 17B, the o-rings 260, 277 prevent fluid from escaping the cylinder 185 through the slots 300.

For a discussion of the linkage 305 used to cause the spool 180 to displace within the cylinder 185, reference is again made to FIGS. 9, 14, 15, 18A-21. As best understood from these figures, the linkage 305 includes the yoke 261 and the pressure control 54. The yoke 261 includes a pair of arms, and each arm has a pivot hole 259 near its free end. The pivot holes 259 pivotally receive therein the free ends of the spool arms 257. The yoke includes an arcuately slotted tongue 310 opposite the yoke arms for pivotally receiving therein a ball 315 extending from the pressure control 54.

As indicated in FIG. 9, in one embodiment, the pressure control 54 is a slide supported by the housing 65 of the handle portion 15 of the irrigator 10. As illustrated in FIGS. 19 and 21, the yoke 261 has a rocker portion 320 from which the tongue 310 extends. As shown in FIGS. 18A and 18B, the rocker portion 320 resides within a hole or slot 325 in the chassis plate 110, which allows the tongue 310 to rock towards the nozzle 20 or towards the base 30, depending on how the slide 54 is displaced along the housing 65.

As indicated in FIG. 18A, when the slide 54 is shifted towards the nozzle 20, the tongue 310 is rocked towards the nozzle 20 thereby causing the yoke 261 to pivot about the hole 325 in the chassis plate 110 such that the yoke arms move towards the base 30 and pull the spool arms 257 towards the base 30, which causes the spool 180 to move towards the base 30 (i.e., the spool 180 moves into the high discharge pressure position). As indicated in FIG. 18B, when the slide 54 is shifted towards the base 30, the tongue 310 is rocked towards the base 30 thereby causing the yoke 261 to pivot about the hole 325 in the chassis plate 110 such that the yoke arms move towards the nozzle 20 and pull the spool arms 257 towards the nozzle 20, which causes the spool 180 to move towards the nozzle 20 (i.e., the spool 180 moves into the low discharge pressure position).

For a discussion regarding the elements of the nozzle release, reference is again made to FIGS. 9, 14, 15 and 18A-20. As illustrated in these figures, the nozzle release button 25 is coupled to a collar 350 having an opening 355 centered about the hole 360 of the nozzle base receiving cylinder 368, which extends from the cylinder outlet 225. The proximal end of the nozzle 20 is received in the receiving cylinder 368 and the collar 350. The collar 350 is biased into a nozzle base groove 370 by a spring 380. The groove 370 extends about the circumference of the nozzle base. To release or disengage the collar 350 from the nozzle base groove 370 to allow the nozzle 20 to be withdrawn from the receiving cylinder 368, the nozzle release button 25 is depressed against the biasing force of the spring 380, which causes the collar 350 to shift out of engagement with the groove 370. The nozzle 20 is then withdrawn from the cylinder 368.

As can be understood from the preceding discussion, the oral irrigator of the present invention is advantageous because it allows a user to adjust the discharge pressure of the fluid stream emanating from the oral irrigator without bringing about a significant change in the pulse rate of the fluid stream. Thus, the oral irrigator can continue to supply a fluid stream at a preferred pulse rate regardless of the discharge pressure selected by the user.

Although the present invention has been described with reference to preferred embodiments, persons skilled in the art will recognize that changes may be made in form and detail without departing from the spirit and scope of the invention. The invention is limited only by the scope of the following claims.

What is claimed is:

1. An oral irrigator comprising
   a fluid reservoir;
   a pumping assembly comprising
      a power source;
      a motor in electrical communication with the power source and including a drive shaft; and
      a pump in fluid communication with the reservoir and connected to the drive shaft; and
   a pressure control assembly in fluid communication with the pump, the pressure control assembly comprising:
      a spool movable from a first position relative to an outlet of the pump to a second position relative to the outlet of the pump, wherein the spool comprises:
         a lumen extending longitudinally along a length of the spool;
         an orifice defined through an outer sidewall of the spool in fluid communication with the lumen: wherein
         in the first position the orifice is aligned with and fluidly connected to the outlet of the pump; and
         in the second position the orifice is misaligned with the outlet of the pump and is not fluidly connected to the pump; and
      a control mechanism operably connected to the spool, wherein movement of the control mechanism in a first direction causes the spool to move in a second direction; and movement of the control mechanism in the second direction causes the spool to move in the first direction; and
   a nozzle in fluid communication with the pressure control assembly; wherein
   when activated, the power source powers the motor, causing the drive shaft to rotate and activate the pump to pump a fluid from the reservoir to the nozzle in a series of pulses at a predetermined pulse rate; and
   the pressure control assembly selectively and mechanically varies a pressure of the fluid exiting the nozzle, maintaining the predetermined pulse rate of the fluid as it exits the nozzle.

2. The oral irrigator of claim 1, wherein the power source provides a substantially constant signal to the motor during operation of the pump.

3. The oral irrigator of claim 1, when activated the motor is driven at a constant speed and the pressure of the fluid exiting the nozzle is selectively variable between a high pressure and a low pressure.

4. The oral irrigator of claim 1, wherein the pressure control assembly varies at least one of the following characteristics to vary the pressure:
   a length of a fluid flow path from an outlet of the pump to the inlet of the nozzle;
   a diameter of a portion of the fluid flow path; or
   a number of direction changes in the fluid flow path.

5. The oral irrigator of claim 4, wherein the pressure control assembly varies the length of the fluid flow path, the at least one diameter of the fluid flow path, and the number of direction changes in the fluid flow path to vary the pressure.

6. The oral irrigator of claim 1, further comprising a housing, wherein the motor is positioned adjacent to the pump.

7. The oral irrigator of claim 6, wherein the power source is positioned above the motor and the pump.

8. The oral irrigator of claim 6, further wherein the power source is positioned below the motor.

9. The oral irrigator of claim 1, further comprising a linkage positioned between the spool and the control mechanism.

10. The oral irrigator of claim 1, wherein the control mechanism and the spool move substantially parallel to a longitudinal length of the nozzle.

11. A water flossing device comprising
    a reservoir;
    a nozzle in fluid communication with the reservoir;
    a pump having an inlet in fluid communication with the reservoir and an outlet in fluid communication with the nozzle;
    a motor connected to the pump and configured to selectively activate the pump;
    a power source in electrical communication with the motor; and
    a pressure assembly connected between the nozzle and the pump, the pressure assembly includes a spool comprising:
       a lumen defined longitudinally along a length of the spool; and
       an orifice defined through a sidewall of the spool and in fluid communication with the lumen;
       a first sealing member connected to the spool and positioned above the orifice; and
       a second sealing member connected to the spool and positioned below the orifice; wherein
    in an on state the power source provides a substantially constant voltage to the motor and the pressure assembly selectively varies an outlet pressure of fluid exiting the nozzle while maintaining a constant pulse rate of the fluid exiting the nozzle, wherein the outlet pressure varies between a high pressure setting and a low pressure setting,
    during the high pressure setting, the spool is in a first position relative to the outlet of the pump and the orifice is fluidly sealed from the outlet of the pump; and
    during the low pressure setting, the spool is in a second position relative to the outlet of the pump and the orifice is in fluid communication with the outlet of the pump and fluid flows through the orifice into the lumen from the outlet of the pump.

* * * * *